United States Patent
Sridhar et al.

(10) Patent No.: US 10,960,209 B2
(45) Date of Patent: Mar. 30, 2021

(54) NEUROMODULATION OF ADRENAL GLAND

(71) Applicants: Galvani Bioelectronics Limited, Middlesex (GB); Case Western Reserve University, Cleveland, OH (US)

(72) Inventors: Arun Sridhar, Stevenage (GB); Corey Smith, Cleveland, OH (US); Kyle Wolf, Cleveland, OH (US); Georgy Zarkua, Cleveland, OH (US); Shyue-An Chan, Cleveland, OH (US)

(73) Assignees: Galvani Bioelectronics Limited, Middlesex (GB); Case Western Reserve University, Cleveland, OH (US)

( * ) Notice: Subject to any disclaimer, the term of this patent is extended or adjusted under 35 U.S.C. 154(b) by 78 days.

(21) Appl. No.: 16/320,288

(22) PCT Filed: Jul. 25, 2017

(86) PCT No.: PCT/EP2017/068805
§ 371 (c)(1),
(2) Date: Jan. 24, 2019

(87) PCT Pub. No.: WO2018/019856
PCT Pub. Date: Feb. 1, 2018

(65) Prior Publication Data
US 2020/0179699 A1     Jun. 11, 2020

Related U.S. Application Data

(60) Provisional application No. 62/366,243, filed on Jul. 25, 2016.

(51) Int. Cl.
*A61N 1/36*     (2006.01)
*A61N 1/05*     (2006.01)

(52) U.S. Cl.
CPC ....... *A61N 1/36082* (2013.01); *A61N 1/0556* (2013.01); *A61N 1/36157* (2013.01); *A61N 1/36171* (2013.01); *A61N 1/36178* (2013.01)

(58) Field of Classification Search
CPC ............. A61N 1/0556; A61N 1/36071; A61N 1/36082; A61N 1/36096; A61N 1/36157; A61N 1/36171; A61N 1/36178
See application file for complete search history.

(56) References Cited

U.S. PATENT DOCUMENTS

| | | |
|---|---|---|
| 2003/0018367 A1 | 1/2003 | Di Lorenzo |
| 2003/0181958 A1 | 9/2003 | Dobak |
| 2004/0230255 A1* | 11/2004 | Dobak, III ......... A61N 1/36085 607/58 |
| 2013/0131746 A1 | 5/2013 | Simon et al. |
| 2016/0015988 A1 | 1/2016 | Perryman |

* cited by examiner

*Primary Examiner* — George Manuel
(74) *Attorney, Agent, or Firm* — Brett A. Lovejoy; Sanjay K. Murthy; Morgan, Lewis & Bockius, LLP

(57) ABSTRACT

Modulation of neural signaling of a branch of the GSN supplying the adrenal gland can regulate the secretion of signaling molecules from the adrenal medulla. In particular, epinephrine, norepinephrine and enkephalin release can be independently regulated.

9 Claims, 17 Drawing Sheets

A

B

Ci

-- -- -- Baseline
——— +Epi

Cii

——— Epi-Baseline

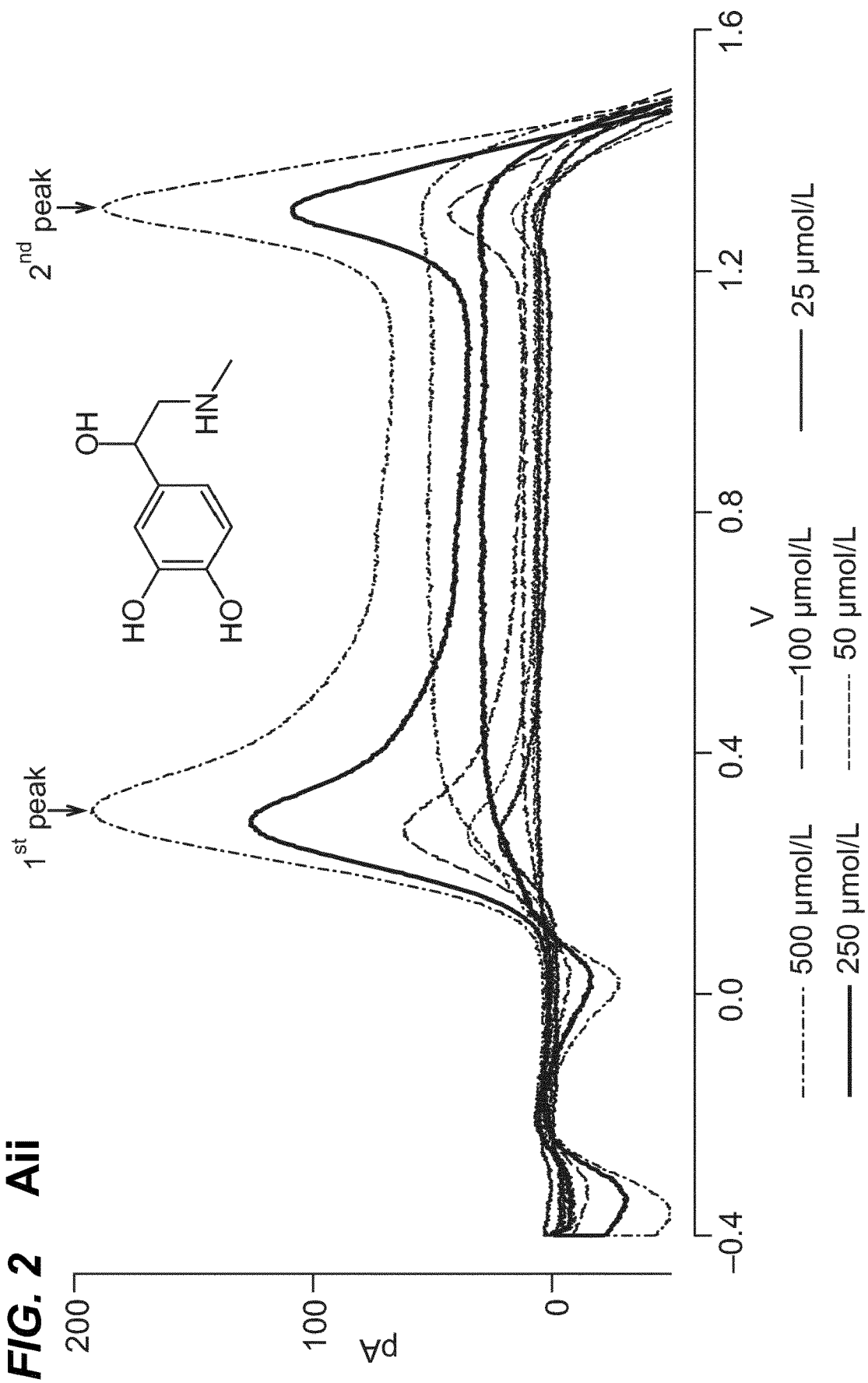
FIG. 2 Aii

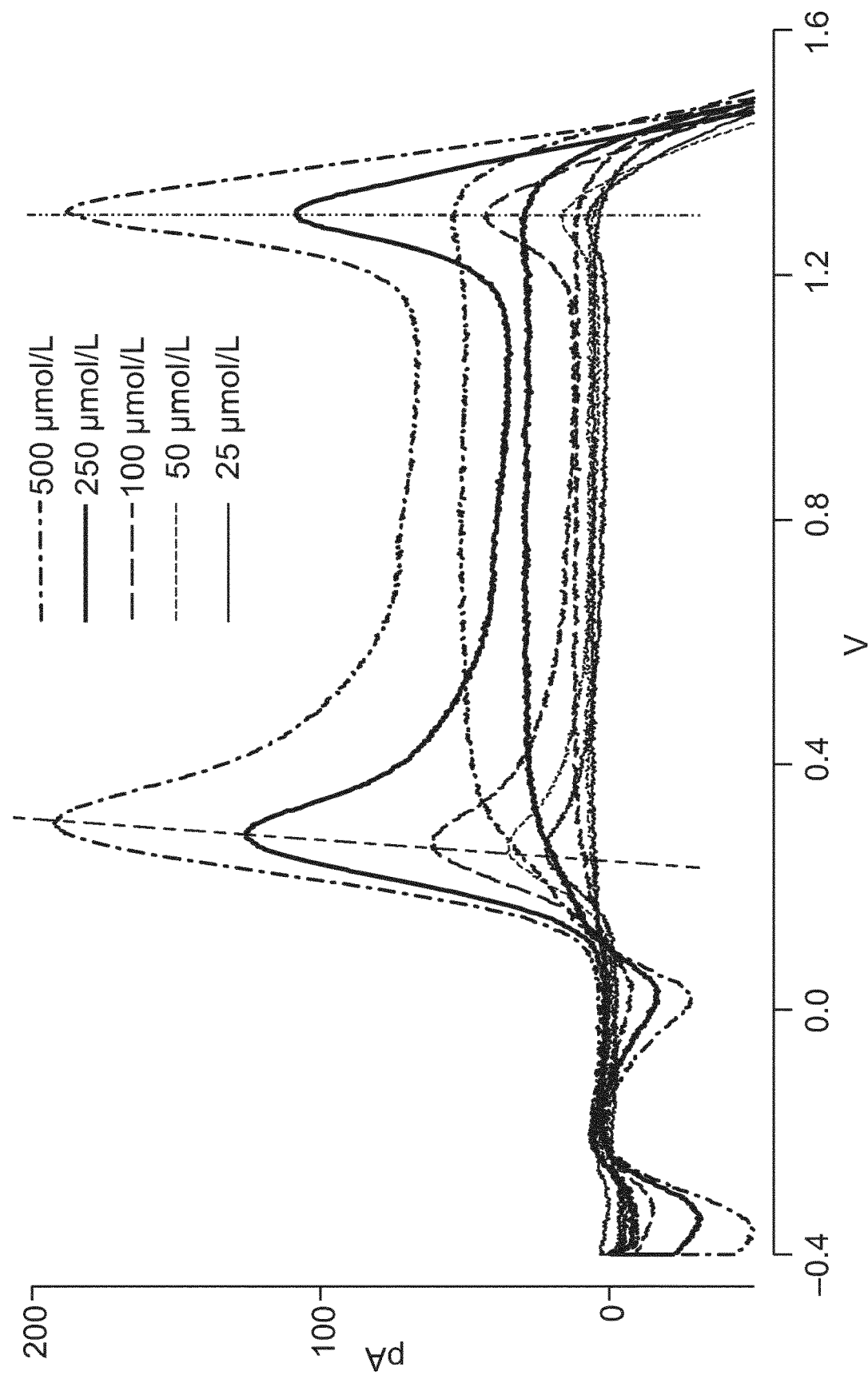
FIG. 3 Aii

A  5 Hz WN

B  AD

C  PD

NEUROMODULATION OF ADRENAL GLAND

This application is filed pursuant to 35 U.S.C. § 371 as a United States National Phase Application of International Patent Application Serial No. PCT/EP2017/068805 filed 25 Jul. 2017, which claims priority to U.S. Application No. 62/366,243 filed 25 Jul. 2016, and the entire contents of each of the foregoing applications are hereby incorporated by reference.

TECHNICAL FIELD

This invention relates to neuromodulation of the adrenal glands. More specifically, the invention relates to medical devices and systems for the modulation of the adrenal glands.

BACKGROUND ART

The adrenal medulla is a primary output of the sympathetic nervous system. It is composed of a highly vascularized cluster of neuroendocrine adrenal chromaffin cells. Upon stimulation through the sympathetic splanchnic nerve, the adrenal chromaffin cells release multiple signaling molecules into the systemic circulation. Examples of the signaling molecules are the regulatory hormones including the catecholamines (e.g. epinephrine (Epi) and norepinephrine (NE)) as well as a host of neuro- and vasoactive peptide transmitters (e.g. enkephalin) (Habib et al., 2001). Together these signaling molecules regulate multiple processes that prepare the body for defense or escape under the acute sympatho-adrenal stress response.

Under homeostatic physiological conditions, the sympathetic nervous system fires at a baseline rate, setting the basal sympathetic tone and working in concert with the parasympathetic nervous system to place the organism into a 'rest and digest' status of energy storage. Under these conditions, adrenal chromaffin cells release modest amounts of catecholamine into the circulation to help regulate physiological functions including shunting of blood to viscera, increasing enteric activity and maintaining basal heart rate.

Emotional or psychological stress, injury or environmental insult initiates the sympathetic 'fight or flight' stress response, leading to a surge in serum catecholamine levels. Thus, perception or even anticipation of danger or harm (anxiety), trauma, pain, hypovolemia from hemorrhage or fluid loss, hypotension, anoxia, extremes of temperature, hypoglycemia, and severe exercise can cause rapid secretion of catecholamines. Under these conditions, NE is released from postganglionic sympathetic nerves throughout the periphery as well as from the adrenal medulla, while Epi is exclusively released from the adrenal medulla (Marley & Prout, 1965; Goldstein et al., 1983; Carmichael & Winkler, 1985; Habib et al., 2001). Specific physiological responses to acute stress, and their signaling molecules from the adrenal medulla, include generalized analgesia (enkephalin), increased cardiac output, blood pressure and blood flow to skeletal muscle (catecholamines, atrial natriuretic factor, neuropeptide Y), elevated blood glucose (epinephrine, pancreastatin) and, under extreme injury or shock, an anticlotting activity (tissue-type plasminogen activator).

The mechanism for the stressor-dependent segregated release of signaling molecules secreted from the adrenal medulla is not understood. Independent regulation of the secretion of signaling molecules from the adrenal gland, especially those from the adrenal medulla, would be useful in therapeutics. It is therefore an object of the invention to modulate adrenal medullary secretion, such as regulating the independent secretion of NE, Epi and enkephalin.

The invention also aims to modulate adrenal medulla output in a way that has minimal impact on basal body function.

The invention also aims to assist in treating conditions associated with impaired control of adrenal medullary secretion, such as impaired catecholamine and/or enkephalin control.

The invention also aims to treat a subject who suffers from, or is at risk of, pathological stress, e.g. by suppressing the catecholamine surge.

SUMMARY OF THE INVENTION

The inventors found that neuromodulation of a branch of the greater splanchnic nerve (GSN) supplying the adrenal gland is capable of modulating adrenal medullary secretion. In particular, neuromodulation of a branch of the GSN supplying the adrenal gland is capable of regulating Epi, NE and enkephalin release independently.

More specifically, the inventors assessed the adrenal medulla output in ex vivo rat preparation after reversible stimulation of the branch of the GSN between the suprarenal ganglion and the adrenal gland. They found that elevated stimulation of the whole branch of the GSN specifically enhances Epi release from the peripheral medulla. Interestingly, elimination of either the posterior or anterior division of that GSN branch from stimulation significantly attenuated Epi release while either division singly can support NE release. They also found that elevated stimulation of the branch of GSN supplying the adrenal gland specifically enhances enkephalin release.

Thus, the invention provides a method of reversibly modulating adrenal medullary secretion in a subject by reversibly modulating neural activity of a branch of the GSN supplying the adrenal gland. A preferred way of reversibly modulating the activity of the branch of the GSN supplying the adrenal gland uses a device or system which applies a signal to the GSN branch. Preferably the branch of the GSN supplying the adrenal gland is modulated between the suprarenal ganglion and the adrenal gland.

The invention also provides a method of modulating adrenal medullary secretion in a subject, comprising applying a signal to a branch of the GSN supplying the adrenal medulla to reversibly modulate the neural activity of the GSN branch.

The invention provides a device or system for reversibly modulating the neural activity of a branch of the GSN supplying the adrenal gland in a subject, preferably the branch of the GSN between the suprarenal ganglion and the adrenal gland, the device or system comprising: at least one transducer suitable for placement on or around: (a) a whole branch of the GSN supplying the adrenal gland, and/or (b) a division of the branch of the GSN between the suprarenal ganglion and the adrenal gland, and a signal generator for generating at least one signal to be applied to the GSN branch and/or division via the at least one transducer such that the at least one signal stimulates the neural activity of the GSN branch and/or division to produce a physiological response in the subject, wherein the physiological response is an increase or decrease in secretion of signaling molecules from the adrenal medulla, and wherein the at least one transducer is at least one electrode, and the signal generator is a voltage or current source configured to generate an electrical signal to be applied to the GSN branch or division via the at least one electrode, and wherein the electrical signal has a frequency of between 1 Hz and 10 Hz.

The invention also provides a device or system for reversibly modulating the neural activity of a branch of the greater splanchnic nerve (GSN) between the suprarenal ganglion and the adrenal gland in a subject, the device or system comprising: a first transducer suitable for placement on or around the anterior division of the GSN branch, a second transducer suitable for placement on or around the posterior division of the GSN branch supplying the adrenal gland, and a signal generator for generating at least one signal to be selectively applied to the GSN branch via the first and/or second transducers respectively such that the at least one signal inhibits or stimulates the neural activity of the GSN branch to produce a physiological response in the subject, wherein the physiological response is an increase or decrease in secretion of signaling molecules from the adrenal medulla.

The invention also provides a method of treating in a subject who suffers from, or is at risk of, pathological stress, comprising (i) implanting in the subject a device or system of the invention; positioning the transducer in signaling contact with the branch of the GSN supplying the adrenal gland; and optionally (iii) activating the device or system.

Similarly, the invention provides a method of reversibly modulating adrenal medullary secretion in a subject, comprising: (i) implanting in the subject a device or system of the invention; (ii) positioning the transducer of the device or system in signaling contact with a branch of the GSN supplying the adrenal gland; and optionally (iii) activating the device or system.

The invention also provides a method of implanting a device or a system of the invention in a subject, comprising: positioning a transducer of the device or system in signaling contact with the branch of the GSN supplying the adrenal gland.

The invention also provides a device or a system of the invention, wherein the device or system is attached to a branch of the GSN supplying the adrenal gland at a site between the suprarenal ganglion and the adrenal medulla.

The invention further provides a neuromodulatory electrical waveform for use in reversibly modulating adrenal medullary secretion, wherein the waveform is comprised of a plurality of pulse trains of square or sawtooth pulses, the plurality of pulse trains delivered at a frequency of between 1 Hz and 10 Hz, such that when applied to a subject's greater splanchnic nerve, preferably the branch of the GSN supplying the adrenal gland between the suprarenal ganglion and the adrenal gland, the waveform stimulates neural activity in the GSN branch.

The invention also provides the use of a neuromodulatory device or system for reversibly modulating adrenal medullary secretion in a subject, by reversibly modulating neural activity in one or both of the anterior or posterior division(s) of the subject's branch of the greater splanchnic nerve (GSN) supplying the adrenal gland.

The invention also provides a charged particle for use in a method of treating a subject who suffers from, or is at risk of, pathological stress, wherein the charged particle causes reversible depolarisation or hyperpolarization of the nerve membrane of a branch of the greater splanchnic nerve (GSN) supplying the adrenal gland, such that an action potential does not propagate through the modified nerve and/or such that an action potential is generated de novo in the modified nerve.

The invention also provides a modified branch of the GSN supplying the adrenal gland to which a transducer of the system or device of the invention is attached. The transducer is in signaling contact with the nerve and so the nerve can be distinguished from the nerve in its natural state. Furthermore, the nerve is located in a subject who suffers from, or is at risk of, pathological stress.

The invention also provides a modified branch of the GSN supplying the adrenal gland, wherein the neural activity is reversibly modulated by applying a signal to the branch of the GSN supplying the adrenal gland between the suprarenal ganglion and the adrenal gland.

The invention also provides a modified branch of the GSN supplying the adrenal gland, wherein the nerve membrane at the region between the suprarenal ganglion and the adrenal gland is reversibly depolarised or hyperpolarised by an electric field, such that an action potential does not propagate through the modified nerve and/or such that an action potential is generated de novo in the modified nerve.

The invention also provides a modified branch of the GSN supplying the adrenal gland bounded by a nerve membrane, comprising a distribution of potassium and sodium ions movable across the nerve membrane to alter the electrical membrane potential of the nerve so as to propagate an action potential along the nerve in a normal state; wherein at least a portion of the nerve between the suprarenal ganglion and the adrenal gland is subject to the application of a temporary external electrical field which modifies the concentration of potassium and sodium ions within the nerve, causing depolarization or hyperpolarization of the nerve membrane, thereby, in a disrupted state, temporarily: (a) blocking the propagation of the action potential across that portion, and/or (b) generating an action potential de novo across that portion; wherein the nerve returns to its normal state once the external electrical field is removed.

The invention also provides a modified branch of the GSN supplying the adrenal gland obtainable by reversibly modulating neural activity of the branch of the GSN supplying the adrenal gland according to a method of the invention.

The invention also provides a method of modifying the activity of a branch of the GSN supplying the adrenal gland, comprising a step of applying a signal to the branch of the GSN supplying the adrenal gland in order to reversibly inhibit the neural activity of the GSN branch in a subject. Preferably the method does not involve a method for treatment of the human or animal body by surgery. The subject already carries a device or system of the invention which is in signaling contact with the GSN branch.

The invention also provides a method of controlling a device or system of the invention which is in signaling contact with the one or both of the anterior and posterior division(s) of the branch of the greater splanchnic nerve (GSN) supplying the adrenal gland, comprising a step of sending control instructions to the device or system, in response to which the device or system applies a signal to the respective one or both of the anterior or posterior division(s) of the branch of the GSN supplying the adrenal gland.

The invention also provides a computer system implemented method, wherein the method comprises applying at least one signal to a branch of the greater splanchnic nerve (GSN) supplying the adrenal gland in a subject, preferably the branch of the GSN between the suprarenal ganglion and the adrenal gland, via at least one transducer that is suitable for placement on or around the GSN branch, such that the at least one signal stimulates or inhibits the neural activity of the GSN branch to produce a physiological response in the subject, wherein the physiological response is an increase or a decrease in secretion of signaling molecules from the adrenal medulla, and wherein the at least one transducer is at least one electrode, and the signal is an electrical signal to be applied to the GSN branch via the at least one electrode, and wherein the stimulation electrical signal has a frequency of between 1 Hz and 10 Hz.

The invention also provides a computer system implemented method, wherein the method comprises applying at least one signal to a branch of the greater splanchnic nerve (GSN) supplying the adrenal gland in a subject, between the suprarenal ganglion and the adrenal gland, via a first transducer suitable for placement on or around the anterior division of the branch of the GSN, and via a second transducer suitable for placement on or around the posterior division of the branch of the GSN, and the at least one signal is selectively applied to the GSN division(s) via the first and/or second transducers respectively such that the at least one signal inhibits or stimulates the neural activity of the GSN division(s) to produce a physiological response in the subject, wherein the physiological response is a decrease or an increase in secretion of signaling molecules from the adrenal medulla.

DETAILED DESCRIPTION OF THE INVENTION

The Greater Splanchnic Nerve Supplying to the Adrenal Gland

The splanchnic nerves carry fibers of the autonomic nervous system (visceral efferent fibers) and sensory fibers from various organs (visceral afferent fibers). All splanchnic nerves carry sympathetic fibers, except for the pelvic splanchnic nerves. The thoracic splanchnic nerves are recognised as medial branches from the lower seven thoracic sympathetic ganglia. They are pre-synaptic nerves of the sympathetic system, and include the GSN, the lesser splanchnic nerve, and the least splanchnic nerve. They pass through the diaphragm to send fibers to the celiac, aorticorenal, and superior mesenteric ganglia and plexuses. Further detail about the thoracic splanchnic nerves and the celiac ganglia are described in Loukas et al. (2010) *Clinical Anatomy* 23:512-22.

The GSN is derived from the fifth to ninth thoracic ganglia in humans, with the potential for contribution from the tenth thoracic ganglia. In most cases, the greater splanchnic nerve originates from four roots, before descending obliquely, giving off branches to the descending aorta and perforating the crus of the diaphragm. There are two GSNs in the human body and, while modulation of either or both is possible according to the invention, the GSN of particular interest is the right GSN.

The adrenal gland on each side is supplied by the GSN. The GSN bifurcates as it leaves the sympathetic chain ganglion, with the anterior division typically smaller in diameter than the posterior division (see FIG. 9). The splanchnic passes through the suprarenal ganglion where it gives rise to a small-diameter fascicle that passes to the celiac ganglion, while the majority of the fibres innervate the adrenal gland. The majority of sympathetic fibres reaching the suprarenal plexus are preganglionic to the medulla.

Thus, the GSN naturally projects sympathetic signals to the adrenal glands. By modulating neural activity in a branch of the GSN supplying the adrenal gland, it is possible to achieve therapeutic effects, such as increasing and/or decreasing adrenal output, thereby assisting in treating conditions associated with impaired catecholamine and/or enkephalin control.

The invention modulates neural activity at or downstream of the suprarenal ganglion, and modulation at a branch of the GSN between the suprarenal ganglion and the adrenal gland is preferred. This branch of the GSN is amenable to surgical intervention and electrode attachment. Ideally, therefore, modulation of neural activity is localised to this branch of the GSN.

Modulation of neural activity prior to the suprarenal ganglion potentially affects signaling to the vasculature, so this may not be desired. Modulation downstream of the suprarenal ganglion towards the celiac ganglia is also less preferable because this would affect signaling of other nerves that contribute to the celiac ganglion and the celiac plexus.

The invention modulates neural activity of the anterior and/or posterior division(s) of the branch of the GSN supplying the adrenal gland between the suprarenal ganglion and the adrenal gland. The invention may modulate the anterior and posterior divisions independently. The invention may inhibit only one division. The invention may stimulate only one division.

The invention may modulate the whole branch of the GSN supplying the adrenal gland between the suprarenal ganglion and the adrenal gland. There are a few ways to configure the electrodes for this setting. For example, this may involve attaching an electrode to both anterior and posterior divisions of the GSN branch between the suprarenal ganglion and the adrenal gland, or attaching an electrode to the branch of the GSN between the suprarenal ganglion and the adrenal gland before or after the splitting of the anterior and posterior divisions. Or this may be involve attaching electrodes separately on each of the anterior and posterior divisions, and the electrodes are stimulated simultaneously.

Modulation of Neural Activity

According to the invention, modulation results in neural activity in at least part of a branch of the GSN supplying the adrenal gland being reduced or increased compared to baseline neural activity in that part of the nerve. This reduction or increased in activity can be across the whole nerve, in which case neural activity is reduced or increased across the whole nerve. Thus inhibition may apply to both afferent and efferent fibers of a branch of the GSN supplying the adrenal gland, but in some embodiments inhibition may apply only to afferent fibers or only to efferent fibers.

As used herein, "neural activity" of a nerve means the signaling activity of the nerve, for example the amplitude, frequency and/or pattern of action potentials in the nerve. The term "pattern", as used herein in the context of action potentials in the nerve, is intended to include one or more of: local field potential(s), compound action potential(s), aggregate action potential(s), and also magnitudes, frequencies, areas under the curve and other patterns of action potentials in the nerve or sub-groups (e.g. fascicules) of neurons therein.

Modulation of neural activity, as used herein, is taken to mean that the signaling activity of the nerve is altered from the baseline neural activity—that is, the signaling activity of the nerve in the subject prior to any intervention. Modulation according to the present invention may involve inhibition of the neural activity of a branch of the GSN supplying the adrenal gland compared to baseline activity. Modulation according to the present invention may involve stimulation of the neural activity of a branch of the GSN supplying the adrenal gland compared to baseline activity. Modulation according to the present invention preferably involves both inhibition and stimulation of the neural activity of a branch of the GSN supplying the adrenal gland compared to baseline activity.

In some cases, the inhibition of neural activity may be a block of neural activity i.e. action potentials are blocked from travelling beyond the point of the block in at least a part of a branch of the GSN supplying the adrenal gland. A block on neural activity is thus understood to be blocking neural activity from continuing past the point of the block. That is, when the block is applied, action potentials may travel along the nerve or subset of nerve fibres to the point of the block, but not beyond the point of the block. Thus, the nerve at the point of block is modified in that the nerve membrane is reversibly depolarised or hyperpolarised by an electric field, such that an action potential does not propagate through the modified nerve. Hence, the nerve at the point of the block is modified in that it has lost its capacity to propagate action potentials, whereas the portions of the nerve before and after the point of block have the capacity to propagate action potentials.

When an electrical signal is used with the invention, the block is based on the influence of electrical currents (e.g. charged particles, which may be one or more electrons in an electrode attached to the nerve, or one or more ions outside the nerve or within the nerve, for instance) on the distribution of ions across the nerve membrane.

At any point along the axon, a functioning nerve will have a distribution of potassium and sodium ions across the nerve membrane. The distribution at one point along the axon determines the electrical membrane potential of the axon at that point, which in turn influences the distribution of potassium and sodium ions at an adjacent point, which in turn determines the electrical membrane potential of the axon at that point, and so on. This is a nerve operating in is normal state, wherein action potentials propagate from point to adjacent point along the axon, and which can be observed using conventional experimentation. One way of characterizing a block of neural activity is a distribution of potassium and sodium ions at one or more points in the axon which is created not by virtue of the electrical membrane potential at adjacent a point or points of the nerve as a result of a propagating action potential, but by virtue of the application of a temporary external electrical field. The temporary external electrical field artificially modifies the distribution of potassium and sodium ions within a point in the nerve, causing depolarization or hyperpolarization of the nerve membrane that would not otherwise occur. The depolarization or hyperpolarization of the nerve membrane caused by the temporary external electrical field blocks the propagation of an action potential across that point, because the action potential is unable to influence the distribution of potassium and sodium ions, which is instead governed by the temporary external electrical field. This is a nerve operating in a disrupted state, which can be observed by a distribution of potassium and sodium ions at a point in the axon (the point which has been blocked) that has an electrical membrane potential that is not influenced or determined by a the electrical membrane potential of an adjacent point.

Block of neural activity encompasses full block of neural activity in the nerve, i.e. there is no neural activity in the whole nerve.

Inhibition may be partial inhibition. Partial inhibition may be such that the total signaling activity of the whole nerve is partially reduced, or that the total signaling activity of a subset of nerve fibres of the nerve is fully reduced (i.e. there is no neural activity in that subset of fibres of the nerve), or that the total signaling of a subset of nerve fibres of the nerve is partially reduced compared to baseline neural activity in that subset of fibres of the nerve. For example a reduction in neural activity of 5%, 10%, 15%, 20%, 25%, 30%, 35%, 40%, 45%, 40%, 50%, 60%, 70%, 80%, 90% or 95%, or blocking of neural activity in a subset of nerve fibres of the nerve. The neural activity may be measured by methods known in the art, for example, by the number of action potentials which propagate through the axon and/or the amplitude of the local field potential reflecting the summed activity of the action potentials.

The invention may selectively block nerve fibres of various sizes within a nerve. Larger nerve fibres tend to have a lower threshold for blocking than smaller nerve fibres. Thus, for example, increasing signal amplitude (e.g. increasing amplitude of an electric signal) may generate block of the smaller fibres.

In some cases, the invention involves stimulation of neural activity. Stimulation of neural activity typically involves increasing neural activity e.g. generating action potentials beyond the point of the stimulation in at least a part of a branch of the GSN supplying the adrenal gland. Stimulation of neural activity is thus understood to be increasing neural activity from continuing past the point of the block. Thus, the nerve at the point of stimulation is modified in that the nerve membrane is reversibly depolarised or hyperpolarised by an electric field, such that a de novo action potential is generated and propagates through the modified nerve. Hence, the nerve at the point of the stimulation is modified in that a de novo action potential is generated. The nerve under stimulation retains the capacity to propagate action potentials.

When an electrical signal is used with the invention, the stimulation is based on the influence of electrical currents (e.g. charged particles, which may be one or more electrons in an electrode attached to the nerve, or one or more ions outside the nerve or within the nerve, for instance) on the distribution of ions across the nerve membrane.

Stimulation of neural activity encompasses full stimulation of neural activity in the nerve—that is, embodiments where the total neural activity is increased in the whole nerve.

Stimulation of neural activity may be partial stimulation. Partial stimulation may be such that the total signaling activity of the whole nerve is partially increased, or that the total signaling activity of a subset of nerve fibres of the nerve is fully increased, or that the total signaling of a subset of nerve fibres of the nerve is partially increased compared to baseline neural activity in that subset of fibres of the nerve. For example an increase in neural activity of 5%, 10%, 15%, 20%, 25%, 30%, 35%, 40%, 45%, 40%, 50%, 60%, 70%, 80%, 90% or 95%, or an increase of neural activity in a subset of nerve fibres of the nerve. The neural activity may be measured by methods known in the art, for example, by the number of action potentials which propagate through the axon and/or the amplitude of the local field potential reflecting the summed activity of the action potentials.

The invention may selectively stimulate nerve fibres of various sizes within a nerve. Larger nerve fibres tend to have a lower threshold for stimulation than smaller nerve fibres. Thus, for example, increasing signal amplitude (e.g. increasing amplitude of an electric signal) may generate stimulation of the smaller fibres as well as larger fibers. For example, asymmetrical (triangular instead of square pulse) waveforms may be used stimulate C-fiber (unmyelinated).

Modulation of neural activity may also be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state.

Modulation of neural activity may comprise altering the neural activity in various other ways, for example increasing or decreasing a particular part of the neural activity and/or stimulating new elements of activity, for example: in particular intervals of time, in particular frequency bands, according to particular patterns and so forth.

One advantage of the invention is that modulation of the neural activity is reversible. Hence, the modulation of neural activity (whether that is an increase, inhibition, block or other modulation of neural activity or change in pattern versus baseline activity) is not permanent. That is, upon cessation of the signal, neural activity in the nerve returns substantially towards baseline neural activity within 1-60 seconds, or within 1-60 minutes, or within 1-24 hours (e.g. within 1-12 hours, 1-6 hours, 1-4 hours, 1-2 hours), or within 1-7 days (e.g. 1-4 days, 1-2 days). In some instances of reversible modulation, the neural activity returns substantially fully to baseline neural activity. That is, the neural activity following cessation of the signal is substantially the same as the neural activity prior to the modulation (i.e. prior to the signal being applied). Hence, the nerve or the portion of the nerve has regained its capacity to propagate action potentials.

In other embodiments, modulation of the neural activity may be substantially persistent. As used herein, "persistent" is taken to mean that the modulated neural activity has a prolonged effect. That is, upon cessation of the signal, neural activity in the nerve remains substantially the same as when signal was being applied—i.e. the neural activity during and following modulation is substantially the same. Reversible modulation is preferred.

Modulation of the neural activity may be (at least partially) corrective. As used herein, "corrective" is taken to mean that the modulated neural activity alters the neural activity towards the pattern of neural activity in a healthy individual, and this is called axonal modulation therapy. That is, upon cessation of modulation, neural activity in the nerve more closely resembles (ideally, substantially fully resembles) the pattern of action potentials in a branch of the GSN supplying the adrenal gland observed in a healthy subject than prior to modulation. Such corrective modulation can be any modulation as defined herein. For example, application of the signal may result in a block on neural activity, and upon cessation of the signal, the pattern of action potentials in the nerve resembles the pattern of action potentials observed in a healthy subject. By way of further example, application of the signal may result in neural activity resembling the pattern of action potentials observed in a healthy subject and, upon cessation of the signal, the pattern of action potentials in the nerve remains the pattern of action potentials observed in a healthy subject. It is hypothesised that such a corrective effect is the result of a positive feedback loop—that is, the underlying disease state is treated as result of the claimed methods, and therefore the chemosensory signals along a branch of the GSN supplying the adrenal gland are not abnormal, and therefore the disease state is not perpetuated by the abnormal activity of the GSN branch.

Modulation of Adrenal Medullary Secretion

Adrenal chromaffin cells differentially secrete signaling molecules, including catecholamine and neuropeptides, as a function of splanchnic input. This activity-dependent differential secretion follows a simple mechanistic regulatory process. Secreted adrenal signaling molecules, catecholamines (either NE or Epi) and neuropeptides, are co-packaged in the same secretory granules (Livett et al., Neuroscience, 1982; 7(5): 1323-1332; Livett et al., Nature 1981; 289: 317-319). Secretion occurs upon granule fusion with the cell surface and the formation of a fusion pore linking the granule lumen with the extracellular space.

Under baseline sympathetic conditions, as defined by the homeostatic 'rest-and-digest' physiological state, chromaffin cells are driven at a low frequency to selectively release freely-soluble catecholamines through a restricted fusion pore.

Under elevated sympathetic drive, as defined by the sympatho-adrenal stress reflex, cells are stimulated at a greatly elevated rate to enhance catecholamine secretion. Moreover, under this heightened stimulation, the mode of exocytic secretion is changed and the fusion pore is actively driven to an expanded state, facilitating release of neuropeptide transmitters from the dense granule core. Furthermore, emerging work indicates activity-dependent control of the degree and duration of fusion pore expansion is responsible for selection among the adrenal-derived neuropeptides. Secretion of specific peptide transmitter species occurs in order of molecular weight and acidity as a function of pore expansion.

Thus, sympathetic activation evokes adrenal neuropeptide release and the degree of sympathetic firing recruits a progression of neuropeptide species to the secretion profile. Enkephalin is the smallest and most soluble adrenal-derived neuropeptide and as such is first to be released upon fusion pore expansion. These findings correlate well with clinical and physiological observations dictating a preferential release of smaller, more soluble peptide transmitters before larger molecular weight peptides [Felmy, F., Traffic, 2007. 8(8): p. 983-97] and more specifically, enkephalin over other adrenal peptides under modest stimulation [Damase-Michel, C., et al., Arch Pharmacol, 1993. 348(4): p. 379-84].

Enkephalin is an endogenous opioid analgesic acting on δ-receptors in pain-sensing peripheral afferent nerves. Enkephalin is well known in the art, and its role and effects on basal body functions is well documented. Enkephalin does not access μ-receptors in the CNS that are associated with opioid desensitization and addiction, thus enkephalin is an effective analgesic while avoiding routes of opioid tolerance and abuse.

The adrenal medulla also secretes catecholamines: Epinephrine (Epi; and also known as adrenalin) and norepinephrine (NE; also known as noradrenalin). These catecholamines and their effects on basal body functions are well documented in the art. They are important for the normal regulation of a variety of bodily functions, including stress reaction, when they cause an increase in blood pressure, the contractility of the heart, and the circulatory level of blood sugar. Removal of the adrenal medulla results in little or no hormonal deficiency because other glands in the body can compensate. By contrast, excessive catecholamine production can be life threatening.

Essentially all the Epi that circulates in the body is derived from the adrenal medulla. In contrast, most of the circulating NE is derived from sympathetic nerve terminals and from the brain, having escaped immediate local re-uptake from synaptic clefts. In the normal adult male about 85% of total catecholamine made by the adrenal medulla is adrenaline, while the remaining 15% being noradrenalin. There is about 1.6 mg of catecholamine present per gram of medulla tissue. The circulating Epi and NE have almost the same effects on the different organs as those caused by direct sympathetic stimulation, except that the effects last 5 to 10 times as long because these hormones are removed from the blood slowly.

The circulating NE causes constriction of essentially all the blood vessels of the body; it causes increased activity of the heart, inhibition of the gastrointestinal tract, dilation of the pupils of the eyes. Epi causes almost the same effects as those caused by NE. However, Epi, because of its greater effect in stimulating the beta receptors, has a greater effect on cardiac stimulation than does NE. For example, Epi causes weak constriction of the blood vessels in the muscles, in comparison with much stronger constriction caused by NE. Because the muscle vessels represent a major segment of the vessels of the body, this difference is of special importance because NE greatly increases the total peripheral resistance and elevates arterial pressure, whereas Epi raises the arterial pressure to a lesser extent but increases the cardiac output considerably more because of its excitatory effect on the heart. Furthermore, Epi has 5-10 times as great a metabolic effect as NE. Indeed the Epi secreted by the adrenal medulla can increase the metabolic rate of the whole body often to as much as 100% above normal, in this way increasing the activity and excitability of the body. It also increases the rate of other metabolic activities such as glycogenlysis in the liver and muscle and glucose release into the blood.

As shown in the example below, the inventors found that there is an overall increased stimulus threshold for Epi release over NE release from the adrenal medulla. Increased stimulation of a branch of the GSN supplying the adrenal gland (e.g. between the suprarenal ganglion and the adrenal gland) specifically increases Epi release from the peripheral adrenal medulla. Elevated Epi release requires concomitant excitation of both divisions of the branch of the GSN supplying the adrenal gland between the suprarenal ganglion and the adrenal gland. Stimulation of either division of that GSN branch singly fails to show enhanced epinephrine release. However, excitation of either single division is largely sufficient to support norepinephrine release. The inventors also found that neuromodulation of either division of the branch of the GSN supplying the adrenal gland between the suprarenal ganglion and the adrenal gland can regulate enkephalin secretion.

Thus, the invention may independently modulate the neural activity of both the anterior and posterior divisions of the branch of the GSN supplying the adrenal gland between the suprarenal ganglion and the adrenal gland. For example, the invention may involve stimulating the anterior and/or posterior divisions, and/or inhibiting the anterior and/or posterior divisions. For example, the invention may involve the following:

Inhibit either the anterior or the posterior division of the branch of the GSN supplying the adrenal gland between the suprarenal ganglion and the adrenal gland to dampen Epi secretion from the adrenal medulla.

Inhibit both the anterior and the posterior divisions of the branch of the GSN supplying the adrenal gland between the suprarenal ganglion and the adrenal gland to dampen NE secretion from the adrenal medulla.

Inhibit the anterior and/or posterior divisions of the branch of the GSN supplying the adrenal gland between the suprarenal ganglion and the adrenal gland to dampen enkephalin secretion from the adrenal medulla.

Stimulate both the anterior and posterior divisions of the branch of the GSN supplying the adrenal gland between the suprarenal ganglion and the adrenal gland to increase Epi secretion from the adrenal medulla.

Stimulate the anterior and/or posterior divisions of the branch of the GSN supplying the adrenal gland between the suprarenal ganglion and the adrenal gland to increase NE secretion from the adrenal medulla.

Stimulate the anterior and/or posterior divisions of the branch of the GSN supplying the adrenal gland between the suprarenal ganglion and the adrenal gland to increase enkephalin secretion from the adrenal medulla.

By stimulating a branch of the GSN supplying the adrenal gland, the adrenal medulla may increase the secretion of a signaling molecule (e.g. Epi, NE or Enkephalin) compared to baseline secretion. For example an increase in secretion by 5%, 10%, 15%, 20%, 25%, 30%, 35%, 40%, 45%, 40%, 50%, 60%, 70%, 80%, 90% 95%, 100%, 150% or 200%.

By inhibiting a branch of the GSN supplying the adrenal gland, the adrenal medulla may decrease the secretion of a signalling molecule (e.g. Epi, NE or Enkephalin) compared to baseline secretion. For example an decrease in secretion by 5%, 10%, 15%, 20%, 25%, 30%, 35%, 40%, 45%, 40%, 50%, 60%, 70%, 80%, 90% or 95%.

Once the signalling molecule is secreted into the circulation, its concentration in circulation is diluted. Stimulation of a branch of the GSN supplying the adrenal gland may result in an increase in the concentration of a signalling molecule in circulation by 5%, 10%, 15%, 20%, 25%, 30%, 35%, 40%, 45%, 40%, 50%, 60%, 70%, 80%, 90%, 95%, 100%, 150% or 200%. Inhibition of a branch of the GSN supplying the adrenal gland may result in a decrease in the concentration of the signalling molecule in circulation by 5%, 10%, 15%, 20%, 25%, 30%, 35%, 40%, 45%, 40%, 50%, 60%, 70%, 80%, 90%, or 95%.

The invention preferably triggers increase and/or decrease in the signalling molecule(s) by a moderate amount. It is considered that a moderate change in the signalling molecule(s) is sufficient to trigger the desired pathological effects. Thus, the invention preferably triggers an increase or a decrease in the secretion of a signalling molecule by ≤50%, ≤40%, ≤30%, ≤20%, or ≤10%. The invention preferably triggers an increase or a decrease in the concentration of a signalling molecule in circulation by ≤50%, ≤40%, ≤30%, ≤20%, or ≤10%.

Application in Therapy

The invention is useful for modulating adrenal medullary secretion in subjects. The invention is useful in treating NE-related pathologies, Epi-related pathologies, and/or enkephalin-related pathologies. The invention is also useful for treating conditions associated with impaired control of adrenal medullary secretion, such as impaired catecholamine and/or enkephalin control.

Thus, the invention is also useful for treating a subject who suffers from, or is at risk of, pathological stress. For example, upon pathological stress, the invention may dampen the release of Epi from the adrenal medulla by inhibiting the anterior or the posterior division of the branch of the GSN supplying the adrenal gland between the suprarenal ganglion and the adrenal gland, thereby suppressing the surge of catecholamines.

For example, acute cold stress selectively elevates NE release (Vollmer, 1996) to constrict peripheral vasculature in order to preserve body heat. Haemorrhage or hypoglycaemia each selectively elevate Epi to stabilize blood pressure, to increase hepatic blood flow, and increase blood glucose through elevated glucagon and decreased insulin sensitivity, respectively (Glaviano et al., 1960; Gerich et al., 1973; Moyer & Mills, 1975; Robertson et al., 1979; Cryer, 1980; Henry, 1992; Vollmer et al., 1992; Krentz et al., 1996;

Vollmer et al., 1997). Other stressors evoke a broader response. For example, acute intermittent hypoxia (a condition found in obstructive sleep apnoea patients), evokes an equivalent increase in both serum NE and Epi (Kumar et al., 2006). In this context, co-release of both catecholamines elevates pulmonary function and cardiac output to increase the supply of oxygen throughout the body. Physical restraint exhibits a more complex response, with acute immobilization initially eliciting an Epi surge, then with repeated restraint both NE and Epi are elevated (Carbonaro et al., 1988; Jeong et al., 2000). Anxiety also exhibits elevated catecholamine levels.

Where the pathology is contributed by a surge in catecholamine levels, the invention is useful in dampening the catecholamines secretion. Conditions associated with a high concentration of Epi includes diabetic ketoacidosis, where the Epi contribute to the pathological state by stimulating glycogenolysis, lipolysis and ketosis.

Abnormal catecholamine concentrations are associated with a variety of diseases, for example hypertonia, pheochromocytoma, sympathetic neuroblastoma, degenerative cardiac diseases, schizophrenia, and alternating psychosis (Manz B. et al. (1990) GIT Labor-Magazin 5/90. 245-254).

Hypersecretion of Epi and NE from tumours of the chromaffin cells (pheochromocytoma) results in a well-defined syndrome. Dramatic clinical episodes are caused by spurts of uncontrolled and excessive catecholamine release. These bursts can result from stress or from a rapid change in posture. Sudden severe headache, palpitations, chest pain, extreme anxiety with a sense of impending death, and cold perspiration may occur. Blood pressure may rise to extremely high levels, for example to 250/150. If Epi is mainly being secreted, the heart rate will be increased. If NE is the predominant hormone, the heart rate will decrease in a reflex response to the marked hypertension. In addition to these episodes, chronic catecholamine excess may product weight loss, as a result of an increased metabolic rate and decreased appetite. Hyperglycemia can result from inhibition of insulin secretion.

The invention is also useful in treatment of any condition responsive to Epi such as cardiac events (e.g. cardiac arrest), and breathing difficulties (e.g. asthma, bronchial asthma, bronchitis, emphysema), respiratory infections, and allergic emergency (e.g. anaphylaxis, asthma, and bronchial asthma). The invention may also be useful in treating Epi-induced hypertension.

The invention is also useful in inducing analgesic effects, e.g. by stimulating enkephalin secretion from the adrenal medulla. An advantage of this is that targeted peripheral adrenal enkephalin release does not access μ-receptors in the CNS that are associated with opioid desensitization and addiction. Thus, the invention is effective in enhancing specificity to analgesia while avoiding routes of opioid tolerance and abuse. This may be useful in treating chronic pain and related syndromes.

The invention may involve detecting one or more signals from the subject. This may be done before, during and/or after modulation of neural activity in a branch of the GSN supplying the adrenal gland.

The signal may be a physiological response indicated by assessing a biomarker indicative of medullary secretion. The biomarker may be the signalling molecules themselves, such as NE, Epi or enkephalin etc, and derivatives and metabolized products thereof.

The biomarker may be any measurable physiological parameter of the effected organ, e.g. the heart. blood pressure For example, the physiological parameters may be heart rate, heart rhythm and heart rate contractility (e.g. ventricular pressure, ventricular contractility, activation-recovery interval, effective refractory period, stroke volume, ejection fraction, end diastolic fraction, stroke work, arterial elastance). Respiration parameters may also be useful, and they can be derived from, for example, a minute ventilation signal and a fluid index can be derived from transthoracic impedance.

Typically, the concentrations of circulating Epi or NE and/or enkephalin are measured when the subject is recumbent and at rest. Urinary excretion of free catecholamines, metanephrines, and vanillylmandelic acid (VMA) may also be measured.

Quantitative changes of signaling molecules secreted from the adrenal medulla can be measured in a living body sample such as urine or plasma. Detection of the circulating biomarkers may be performed directly on a sample taken from a subject, or the sample may be treated between being taken from a subject and being analysed. For example, a blood sample may be treated by adding anti-coagulants (e.g. EDTA), followed by removing cells and cellular debris, leaving plasma containing the biomarkers for analysis. Alternatively, a blood sample may be allowed to coagulate, followed by removing cells and various clotting factors, leaving serum containing the biomarkers for analysis.

Numerous methods are available in the art for the determination of catecholamines: fluorometric assays, radio enzymatic assays (REA), high-performance liquid chromatography (HPLC) in combination with different detection techniques, gas chromatography with mass spectrometric detection (GC-MS), radio immunoassays (RIA) and enzyme immunoassays (EIA) (Manz B. et al. (1990) GIT Labor-Magazin 5/90, 245-254; Wolthers B. G. et al. (1997) Clinical Chemistry 43, 114-120). Further analytical methods include colorimetry (Baron et al. Anal. Chem. 2005; 77(6):1566-1571), liquid chromatography-mass spectrometry (Thomas et al. 2006; 64(9-10):587-5912006), potentiometry with ion-sensitive field effect transistors (Kharitonov et al. Anal Chem. 1999 Dec. 1; 71(23):5441-3), and amperometry. Electrochemical sensors can also be used, and these are reviewed in Özel et al. (Anal Lett. 2015 May 3; 48(7): 1044-1069.)

Effectiveness of therapy can be assessed in various ways, but typically involves an improvement in one or more detected physiological parameters (e.g. one or more of the biomarkers mentioned above), i.e. the value of the parameter in the subject is changed towards the normal value or normal range for that value.

As used herein, a measurable physiological parameter is detected in a subject when the value for that parameter exhibited by the subject at the time of detection is determined. A detector is any element able to make such a determination.

In certain embodiments, the invention further comprises a step of detecting one or more physiological parameters of the subject, wherein the signal is applied only when the detected physiological parameter meets or exceeds a predefined threshold value. The physiological parameter may be any parameter described herein.

In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuroinhibitory device/system, the device/system further comprises at least one detector configured to detect the one or more physiological parameters.

A "predefined threshold value" for a physiological parameter is the minimum (or maximum) value for that parameter that must be exhibited by a subject or subject before the specified intervention is applied. For any given parameter, the threshold value may be defined as a value indicative of a pathological state or a disease state, or as a value indicative of the onset of a pathological state or a disease state. Thus, depending on the predefined threshold value, the invention can be used as a prevention or a treatment. Alternatively, the threshold value may be defined as a value indicative of a physiological state of the subject (that the subject is, for example, asleep, post-prandial, or exercising). Appropriate values for any given parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that parameter than the predefined threshold value.

For example, basal plasma Epi level is 25-50 pg/ml ($6 \times 10^{-10}$M). The estimated daily basal delivery rate of Epi is 150 µg. Thus, when the circulating Epi concentration is at a level abnormally above the baseline (e.g. above 200 pg/ml) electrical block to either the anterior or the posterior division of the branch of the GSN supplying the adrenal gland is applied to dampen the secretion of Epi into the blood circulation. When the Epi concentration is at a level abnormally below the baseline (e.g. below 20 pg/ml), electrical stimulation to both the anterior and posterior divisions of the branch of the GSN supplying the adrenal gland is applied to increase the secretion of Epi into the blood circulation.

Preferably, for regulation of the catecholamine release from the adrenal medulla, the invention involves a closed-loop system. Hence, the stimulation or inhibition of a branch of the GSN supplying the adrenal gland is controlled by the physiological parameter. Devices and systems appropriate for this are explained further below.

For regulation of encephalin release from the adrenal medulla, the invention preferably involves a closed-loop or an open-loop system. The closed-loop system may involve the stimulation or inhibition of a branch of the GSN supplying the adrenal gland controlled by the physiological parameter. The open-loop system is typically where the stimulation or inhibition of a branch of the GSN supplying the adrenal gland is controlled by an operator, who may be the subject itself or a clinical practitioner. Hence, in this embodiment, circulation encephalin level is controlled on demand. Devices and systems appropriate for these embodiments are explained further below.

The invention can be used in combination with conventional catecholamine agonists and antagonists. For example, a group of agonists called amphetamines are used as nasal decongestants, appetite suppressants, and general stimulants. However, amphetamines may cause hypertension, exacerbate tachycardia, palpitations, and nervousness in hyperthyroid patients, or increase plasma glucose in diabetic patients. In large doses, they can product life-threatening "highs". Certain beta agonists are used to quiet premature uterine contractions in pregnancy. Thus, the invention can be used in combination with administering a catecholamine agonist or antagonist. The invention also provides a catecholamine agonist or antagonist for use in treating a subject, wherein the subject has an implanted device/system of the invention in signaling contact with a branch of the GSN supplying the adrenal gland.

An Implantable Device/System for Implementing the Invention

An implantable device according to the invention comprises at least one transducer, preferably an electrode, suitable for placement on or around a branch of the GSN supplying the adrenal gland, preferably between the suprarenal ganglion and the adrenal gland. The device/system preferably also comprises a controller coupled to the at least one transducer. The various components are preferably part of a single physical device. As an alternative, however, the invention may use a system in which the components are physically separate, and communicate wirelessly. Thus, for instance, the transducer and the controller can be part of a unitary device, or together may form a system (and, in both cases, further components may also be present to form a larger device or system e.g. a power source, a sensor, etc.).

Electrodes

Electrodes capable of controlling delivery of current to a nerve cell in order to affect the signals passing along the nerve fiber are known in the art. US 2015/0174397 A1 discloses several types of electrode for non-damaging neural tissue conduction block. The document discloses cuff electrodes (e.g. spiral cuff, helical cuff or flat interface), and flat interface electrodes, both of which are also suitable for use with the present invention. A mesh, a linear rod-shaped lead, paddle-style lead or disc contact electrode (including multi-disc contact electrodes) are also disclosed in US 2015/0174397 A1 and would be suitable for use in the present invention. Also suitable are intrafascicular electrode, glass suction electrode, paddle electrode, bipolar hemi-cuff electrode, bipolar hook electrode, percutaneous cylindrical electrode. Electrodes may be monopolar, bipolar, tripolar, quadripolar or have five or more poles. The electrodes may fabricated from, or be partially or entirely coated with, a high charge capacity material such as platinum black, iridium oxide, titanium nitride, tantalum, poly(elthylenedioxythiophene) and suitable combinations thereof.

US 2011/0160798 discloses separated-interface nerve electrodes, and in particular forms of ionic coupling electrodes (for example in the form of a cuff electrode) that facilitates the application of a prolonged single phase current to a nerve which mitigates the kind of nerve damage described elsewhere herein. This kind of electrode would be suitable for use in the present invention.

US 2011/0125216 discloses adjustable nerve electrodes, particularly suited for nerve block by delivery of high frequency alternating current (HFAC). The electrodes comprises two or more contacts and logic configured to selectively control the application of HFAC signals through the two or more contacts, in order to control onset response. This kind of electrode would also be suitable for use in the present invention, particularly in combination with delivery of a HFAC or KHFAC signal.

Similar disclosures concerning other neural modulation techniques, such as neural stimulation as well as neural inhibition or block are also known in the art, as described elsewhere herein.

In the examples disclosed elsewhere herein, certain types of electrode have been used for controlling delivery of specific types of signal. In one example, a platinum/iridium parallel bipolar electrode, (FHC, Bowdoin, Me., USA) was used to deliver stimuli to the nerve, whereas in another a multi-pole cuff electrode (CorTec; Freiburg Germany) was used. Both parallel bipolar and cuff electrodes limit leakage of the current and prevent stimulation of adjacent nerves compared to stimulation through unipolar electrodes and tissue grounds.

The signal electrodes are configured to be placed near, attached to or implanted within the nerve.

For an AC signal, the device may use a single phase signal, and therefore provide a single signal electrode, with a ground electrode provided either near, attached to or implanted within the nerve (i.e. in close proximity to the signal electrode) or remote from, even external to the subject. Alternatively, the device may comprise a biphasic signal, wherein two signal electrodes are provided 180° out of phase, both placed near, attached to or implanted within the nerve and in close proximity to each other.

For a DC signal, one or more signal electrodes may be provided. The electrodes may be bipolar and placed (e.g.) either side of a nerve or otherwise in close proximity, in which case the DC current may flow between the electrodes. Alternatively, the electrodes may be monopolar, in which case the DC current may flow from the signal electrode to a remote ground electrode provided either near, attached to or implanted within the nerve (i.e. in close proximity to the signal electrode) or remote from, even external to the subject.

A specific form of electrode (referred to herein as a carousel electrode) is disclosed in US 2015/0174397. The electrode has multiple electrode contacts for contacting the nerve. In one embodiment, four contiguous monopolar electrode contacts is provided. As described in that document, the carousel electrode is operated by continuously cycling DC pulses across the plurality of electrode contacts.

Suitable Forms of an Electrical Signal

Signals applied according to the invention are ideally non-destructive. As used herein, a "non-destructive signal" is a signal that, when applied, does not irreversibly damage the underlying neural signal conduction ability of the nerve. That is, application of a non-destructive signal maintains the ability of a branch of the GSN supplying the adrenal gland (or fibres thereof, or other nerve tissue to which the signal is applied) to conduct action potentials when application of the signal ceases, even if that conduction is in practice artificially modulated, such as stimulated, inhibited or blocked as a result of application of the non-destructive signal.

The signal will usually be an electrical signal, which may be, for example, a voltage or current. In certain such embodiments the signal applied comprises a direct current (DC), such as a charge balanced direct current, or an alternating current (AC) waveform, or both a DC and an AC waveform. Characteristics of stimulating and inhibitory, including blocking, electrical waveforms for use with the invention are described in more detail below. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. However, electrical signals are just one way of implementing the invention, and other suitable signals are described below.

The use of an electrical signal is preferred over other forms of signal, such as ultrasound or heat because electrical signals produce minimal agitation. Ultrasound or heat signals tend to agitate the adrenal gland, which would cause dumping of large amounts of catecholamines into the circulation.

A combination of charge balanced DC and AC is particularly useful for mitigating the onset response that is typical of AC, particularly KHFAC signals. In these cases, a DC signal, which does not induce an onset response, is applied for a short initial period to block the nerve, during or after which an AC signal is introduced (e.g. see Franke et al. J Neural Eng 2014; 11(5):056012.). WO 2009/058258 discloses an onset-mitigating high frequency nerve block, wherein a ramped DC nerve block signal is applied to the nerve, followed by application of a HFAC nerve block. Such a signal may be used with the present invention.

Conduction block using electrical signals (e.g. AC and DC signals) is produced by creating a finite region of axons through which action potentials cannot pass. This region is positioned directly under the electrode and generally extends longitudinally a few millimeters. Thus, the block effect is isolated to the immediate vicinity of the blocking electrode, with no systemic effects.

A unique characteristic of the block is the rapid reversibility of the block when the signal is terminated. Typically, reversibility is demonstrated where the level of adrenal medullary secretion returns to the pre-block values.

A few hypotheses have been put forward for the mechanism by which these electrical signals block nerve conduction (Kilgore et al., Neuromodulation 2014; 17(3): 242-255). One early explanation was the accumulation of extracellular potassium. The second more recent proposal has been that outward potassium currents overwhelm the inward sodium currents at the nodes or axon section (in unmyelinated axons) influenced by the KHFAC and produce block. The third hypothesis has recently gained traction and it focuses on sodium channel inactivation as the cause of KHFAC block. Animal model studies demonstrated that KHFAC resulted in an increased inward sodium current compared to the outward potassium current, leading to a dynamic membrane depolarisation of a number of nodes under the electrode. This depolarization led to the inactivation of about 90% of the sodium channels in the node directly under the electrode. Regardless of the mechanism, application of electrical signals are effective in blocking neural activity.

In certain embodiments the DC waveform or AC waveform may be a square, sinusoidal, triangular or complex waveform. The DC waveform may alternatively be a constant amplitude waveform. In certain embodiments the electrical signal is an AC sinusoidal waveform.

The electric signal may be applied as step change or as a ramp change in current or intensity.

It will be appreciated by the skilled person that the current amplitude of an applied electrical signal necessary to achieve the intended neuromodulation or neuroinhibitory will depend upon the positioning of the electrode and the associated electrophysiological characteristics (e.g. impedance). It is within the ability of the skilled person to determine the appropriate current amplitude for achieving the intended neuromodulation or neuroinhibitory in a given subject. For example, the skilled person is aware of methods suitable to monitor the neural activity profile induced by neuromodulation or neuroinhibitory.

Examples of Implantable Devices

In examples according to the invention, an implantable system is provided, comprising one or more electrodes attachable to (i.e. for placement on or around) a branch of the GSN supplying the adrenal gland. Various embodiments, described in more detail below, may be utilized in order to (for example) increase or dampen secretion of one or more signaling molecules secreted from the adrenal medulla, specifically Epi, NE and enkephalin.

In some embodiments, increasing or dampening secretion of the signaling molecules is achieved by inhibiting or stimulating one of the anterior or posterior divisions of the branch of the GSN supplying the adrenal gland between the suprarenal ganglion and the adrenal gland. In other embodiments, increasing or dampening secretion of the signaling molecules is achieved by inhibiting or stimulating the whole branch of the GSN supplying the adrenal gland between the suprarenal ganglion and the adrenal gland, which may be achieved either by inhibiting or stimulating both divisions independently (but simultaneously), or by inhibiting or stimulating both divisions together, or by inhibiting or stimulating the whole GSN above or below the divisions.

Inhibiting and stimulating a branch of the GSN supplying the adrenal gland may be done using electrodes. Where it is required to inhibit or stimulate of one of the divisions independently of the other, this may be achieved by placing an electrode on or around just one division, or one electrode on or around each division. Where it is required to inhibit or stimulate the whole branch of the GSN supplying the adrenal gland between the suprarenal ganglion and the adrenal gland, this may be achieved by placing an electrode on or around a branch of the GSN supplying the adrenal gland above or below the divisions, or by placing an electrode on or around both divisions, or by placing an electrode on or around each branch.

Example 1

An implantable system according to Example 1 comprises a first electrode attachable to (i.e. for placement on or around) the anterior division of the branch of the GSN supplying the adrenal gland between the suprarenal ganglion and the adrenal gland and a second electrode attachable to the posterior division of the branch of the GSN supplying the adrenal gland between the suprarenal ganglion and the adrenal gland. The electrodes are platinum/iridium parallel bipolar electrodes (FHC, Bowdoin, Me., USA), but multipole cuff electrode (CorTec; Freiburg Germany) may be used instead. The electrodes can be the same, or different.

The implantable system comprises a signal generator coupled to the first and second electrodes and capable of delivering a) an electrical signal to both electrodes to deliver that signal to each division independently; and/or b) a first electrical signal to the first electrode to deliver the first signal to the anterior division and a second, different, electrical signal to the second electrode to deliver the second signal to the posterior division. In the latter case, it is also contemplated that the signal generator may be configured to deliver a signal to one of the first or second electrodes, whilst not delivering a signal to the other. This configuration allows the implantable system to deliver a signal to one or both division(s) of the branch of the GSN supplying the adrenal gland between the suprarenal ganglion and the adrenal gland either together or independently of the other.

Example 2

An implantable system according to Example 2 comprises at least one electrode attachable to (i.e. for placement on or around) both the anterior and posterior divisions of the branch of the GSN supplying the adrenal gland between the suprarenal ganglion and the adrenal gland. The electrode may be as in Example 1, or different.

The implantable system comprises a signal generator coupled to the electrodes and capable of delivering an electrical signal to the electrode to deliver that signal to both divisions of the branch of the GSN supplying the adrenal gland between the suprarenal ganglion and the adrenal gland together, and thus to the whole branch of the GSN supplying the adrenal gland between the suprarenal ganglion and the adrenal gland.

In a modified version of Example 2, the at least one electrode is attachable to (i.e. for placement on or around) to the GSN above or below the divisions to deliver the signal to the branch of the GSN supplying the adrenal gland between the suprarenal ganglion and the adrenal gland.

Example 3

An implantable system according to Example 3 comprises first and second electrodes, in accordance with those of Example 1, and a third electrode in accordance with either of those in Example 2.

The implantable system further comprises a signal generator coupled to the electrodes and capable of delivering electrical signals to either or the both division(s) of the branch of the GSN supplying the adrenal gland between the suprarenal ganglion and the adrenal gland independently, and to the whole branch of the GSN supplying the adrenal gland between the suprarenal ganglion and the adrenal gland. The signal generator may be configured to deliver a signal to one of the first or second electrodes, whilst not delivering a signal to the other, and also to deliver a signal to the third electrode whilst not delivering a signal to one or both of the first and second electrodes. This configuration allows the implantable system to deliver a signal to one or both division(s) of the branch of the GSN supplying the adrenal gland between the suprarenal ganglion and the adrenal gland either together or independently of the other, and to the whole branch of the GSN supplying the adrenal gland between the suprarenal ganglion and the adrenal gland.

Example 4

An implantable system according to Example 4 comprises an electrode attachable to (i.e. for placement on or around) the anterior or the posterior division of the branch of the GSN supplying the adrenal gland between the suprarenal ganglion and the adrenal gland. The electrode may be as in Example 1, or different. The implantable system comprises a signal generator coupled to the electrode and capable of delivering an electrical signal to the electrode to deliver that signal to the division of the branch of the GSN supplying the adrenal gland between the suprarenal ganglion and the adrenal gland.

Examples of Delivering Signals to the GSN Supplying the Adrenal Gland

In all of the above examples, the signal generator may be configured to deliver a signal for stimulating the respective part(s) of a branch of the GSN supplying the adrenal gland, and/or a signal for inhibiting the respective part(s) of a branch of the GSN supplying the adrenal gland. Depending upon application, the signal generator may be configured to deliver a stimulating and/or inhibiting signal to any or all of the electrodes mentioned in the above examples. For instance, the signal generator may be configured to deliver a stimulating signal to both electrodes of Example 1, the one or more electrodes of Example 2, or all three electrodes of Example 3. Alternatively, or in addition, the signal generator may be configured to deliver an inhibitory signal to both electrodes of Example 1, the one or more electrodes of Example 2, or all three electrodes of Example 3. In one preferred arrangement, the signal generator is able to deliver an inhibitory signal to either one of the first and second electrodes of Example 1, and to deliver a stimulating signal to both of the first and second electrodes together.

As described elsewhere herein, devices according to the invention may advantageously be configured to do one or more of the following:

- Inhibit either the anterior or the posterior division of the branch of the GSN supplying the adrenal gland between the suprarenal ganglion and the adrenal gland (e.g. via the first or second electrode, respectively, of Example 1 above; or via the electrode in Example 4 above) to dampen Epi secretion from the adrenal medulla.
- Inhibit both the anterior and the posterior divisions of the branch of the GSN supplying the adrenal gland between the suprarenal ganglion and the adrenal gland (e.g. via the first and second electrodes, respectively, of Example 1 above, or via the electrode of Example 2 above) to dampen NE secretion from the adrenal medulla.
- Inhibit the anterior and/or posterior division(s) of the branch of the GSN supplying the adrenal gland between the suprarenal ganglion and the adrenal gland (e.g. via the first and/or second electrodes, respectively, of Example 1 above, or via the electrode of Example 2, above) to dampen enkephalin secretion from the adrenal medulla.
- Stimulate both the anterior and posterior divisions of the branch of the GSN supplying the adrenal gland between the suprarenal ganglion and the adrenal gland (e.g. via the first and second electrodes, respectively, of Example 1 above, or via the electrode of Example 2 above) to increase Epi secretion from the adrenal medulla.
- Stimulate the anterior and/or posterior division(s) of the branch of the GSN supplying the adrenal gland between the suprarenal ganglion and the adrenal gland (e.g. via the first and/or second electrodes, respectively, of Example 1 above, or via the electrode of Example 2, above) to increase NE secretion from the adrenal medulla.
- Stimulate the anterior and/or posterior division(s) of the branch of the GSN supplying the adrenal gland between the suprarenal ganglion and the adrenal gland (e.g. via the first and/or second electrodes, respectively, of Example 1 above, or via the electrode of Example 2, above) to increase enkephalin secretion from the adrenal medulla.

In a particularly preferred arrangement, an implantable device is provided according to Example 1 above, wherein the signal generator is configured to provide a stimulating signal to either the first or second electrode exclusively, and to provide an inhibitory signal to both electrodes together.

Stimulating Signal

Stimulation of a branch of the GSN supplying the adrenal gland can be achieved using electrical signals which serve to replicate the normal neural activity of the GSN branch. Preferred embodiments of the stimulating signal comprise a plurality of temporally separated pulse trains, each pulse train being made up of a plurality of pulses. The pulses are 10 µs in duration, though their duration may be between 1 µs and 60 µs, preferably between 3 µs and 30 µs, more preferably between 5 µs and 15 µs.

The signal generator is configured to deliver the plurality of pulse trains at frequencies of between 1 Hz and 10 Hz (i.e. between 1 pulse train per second and 10 pulse trains per second). Frequencies of 1 Hz, 5 Hz and 10 Hz are preferred, though any frequency within the range may be chosen.

The signal generator is configured to deliver pulses at a constant current of 200 µA, though the current may be between 100 µA and 300 µA, preferably between 150 µA and 250 µA, more preferably between 175 µA and 225 µA.

The signal generator is configured to deliver the signal (comprising a plurality of pulse trains) for a period of 60 seconds, though the duration may be between 30 seconds and 90 seconds, preferably between 45 seconds and 75 seconds.

The signal generator may be pre-programmed to deliver one or more pre-defined signals with parameters falling within the range given above. Alternatively, the signal generator may be controllable to adjust one or more of the parameters, namely pulse duration, pulse train frequency, pulse current amplitude, signal duration. Control may be open loop, wherein the user or operator of the implantable device may configure the signal generator using an external controller, or control may be closed loop, wherein signal generator modifies the signal parameters in response to sensed physiological signals.

Inhibitory Signal

Inhibition of GSN activity can be achieved using electrical signals which are applied via one or more transducers placed in signaling contact with a branch of the GSN supplying the adrenal gland. An inhibitory signal can take various forms, for example, a voltage or current. In certain such embodiments the signal applied comprises a direct current (DC), such as a charge balanced direct current, or an alternating current (AC) waveform, or both a DC and an AC waveform. Characteristics of inhibitory electrical waveforms for use with the invention are described in more detail below. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. A combination of charge balanced DC and AC is particularly useful, with the DC being applied for a short initial period after which only AC is used (e.g. see Franke et al. 2014, *J Neural Eng* 11(5):056012).

In certain embodiments, the electrical signal has a frequency of 0.5 to 100 kHz, optionally 1 to 50 kHz, optionally 5 to 50 KHz. In certain embodiments the signal has a frequency of 25 to 55 kHz, optionally 30 to 50 kHz. In certain embodiments, the signal has a frequency of 5-10 KHz. In certain embodiments, the electrical signal has a frequency of greater than 1 kHz. In certain embodiments, the electrical signal has a frequency of greater than 20 kHz, optionally at least 25 kHz, optionally at least 30 kHz. In certain embodiments the signal has a frequency of 30 kHz, 40 kHz or 50 kHz.

Before becoming inhibitory, electrical signaling can be preceded by a short period in which the nerve is instead stimulated (an "onset response" or "onset effect"). Various ways of avoiding an onset response are available. In certain embodiments, an onset response as a result of the signal being applied can be avoided if the signal does not have a frequency of 20 kHz or lower, for example 1-20 kHz, or 1-10 kHz. Frequency- and amplitude-transitioned waveforms to mitigate onset responses in high-frequency nerve blocking are described by Gerges et al. 2010 (*J. Neural Eng.* 7:066003). Amplitude ramping can also be used, as discussed by Bhadra et al. 2009 (DOI: 10.1109/IEMBS.2009.5332735), or a combination of KHFAC with charge balanced direct current waveforms can be used (Franke et al. 2014, *J Neural Eng* 11(5):056012). A combination of KHFAC and infra-red laser light ('ACIR') has also been used to avoid onset responses (Lothet et al. 2014, *Neurophotonics* 1(1):011010).

In certain embodiments, the electrical signal has a current of 0.1-10 mA, optionally 0.5-5 mA, optionally 1 mA-2 mA, optionally 1 mA or 2 mA.

In certain embodiments, the signal is an electrical signal comprising an AC sinusoidal waveform having a frequency of greater than 25 kHz, optionally 30 to 50 kHz. In certain such embodiments, the signal can be an electrical signal comprising an AC sinusoidal waveform having a frequency of greater than 25 kHz, optionally 30 to 50 kHz having a current of 1 mA or 2 mA.

Some electrical forms of neuromodulation may use direct current (DC), or alternating current (AC) waveforms applied to a nerve using one or more electrodes. A DC block may be accomplished by gradually ramping up the DC waveform amplitude (Bhadra & Kilgore, IEEE Transactions on Neural systems and rehabilitation engineering, 2004 12:313-324).

Some other AC techniques include HFAC or KHFAC (high-frequency or kilohertz frequency) to provide a reversible block (for example see Kilgore & Bhadra, 2004, Medical and Biological Engineering and Computing, May; 42(3): 394-406. Nerve conduction block utilising high-frequency alternating current). In the work of Kilgore & Bhadra, a proposed waveform was sinusoidal or rectangular at 3-5 kHz, and typical signal amplitudes that produced block were 3-5 Volts or 0.5-2.0 milliAmperes peak-to-peak. Further details of charge-balanced KHFAC, which can be used with the invention, are discussed by Kilgore & Bhadra (2014) *Neuromodulation* 17:242-55. Advantageously, KHFAC is reversible.

HFAC may typically be applied at a frequency of between 1 and 50 kHz at a duty cycle of 100% (Bhadra et al., Journal of Computational Neuroscience, 2007, 22:313-326). Methods for selectively blocking activity of a nerve by application of a waveform having a frequency of 5-10 kHz are described in U.S. Pat. No. 7,389,145. Similarly, U.S. Pat. No. 8,731,676 describes a method of ameliorating sensory nerve pain by applying a 5-50 kHz frequency waveform to a nerve.

Some commercially available nerve blocking systems include the Maestro™ system available from Enteromedics Inc. of Minnesota, USA. Similar neuromodulation devices are more generally discussed in US2014/0214129 and elsewhere.

Other Suitable Forms of Transducer and Signal

Optogenetics is a technique in which genetically-modified cells express photosensitive features, which can then be activated with light to modulate cell function. Many different optogenetic tools have been developed for inhibiting neural firing. A list of optogenetic tools to suppress neural activity has been compiled (Ritter L M et al., 2014 *Epilepsia* doi: 10.1111/epi.12804.). Acrylamine-azobenzene-quaternary ammonium (AAQ) is a photochromic ligand that blocks many types of K+ channels and in the cis configuration, the relief of K+ channel block inhibits firing (Nat Neurosci. 2013 July; 16(7):816-23. doi: 10.1038/nn.3424. Optogenetic pharmacology for control of native neuronal signaling proteins. Kramer R H et al, which is incorporated herein by reference). Thus light can be used with genetic modification of target cells to achieve inhibition of neural activity, particularly in pre-clinical settings.

Microprocessor

The implantable device may comprise a microprocessor. The microprocessor may be responsible for triggering the beginning and/or end of the signals delivered to a branch of the GSN supplying the adrenal gland by the at least one transducer. Optionally, the microprocessor may also be responsible for generating and/or controlling the parameters of the signal. A pulse generator with a processor configuration suitable for nerve stimulation applications is disclosed in ref.14.

The microprocessor may be configured to operate in an open-loop fashion, wherein a pre-defined signal (e.g. as described above) is delivered to a branch of the GSN supplying the adrenal gland, preferably between the suprarenal ganglion and the adrenal gland at a given periodicity (or continuously) and for a given duration (or indefinitely) with or without an external trigger, and without any control or feedback mechanism. Alternatively, the microprocessor may be configured to operate in a closed-loop fashion, wherein a signal is applied based on a control or feedback mechanism. As described elsewhere herein, the external trigger may be an external controller operable by the user or operator to initiate delivery of a signal.

The microprocessor of the device may be constructed so as to generate, in use, a preconfigured and/or user-selectable signal that is independent of any input. Preferably, however, the microprocessor is responsive to an external signal, more preferably information pertaining to a physiological response in the subject.

The implantable device of the present invention may comprise circuitry to detect physiological signals indicative of the levels of signaling molecules secreted from the adrenal medulla, and use these signals to trigger the microprocessor to deliver a signal of the kinds described above (for example in Examples 1, 2, 3 and 4 above) to a branch of the GSN supplying the adrenal gland using the at least one transducer.

Upon receipt of signals received from the one or more sensors, the processor may calculate the current levels of signaling molecules secreted from the adrenal medulla in accordance with techniques known in the art.

The device may comprise memory for storing physiological data pertaining to normal levels of signaling molecules secreted from the adrenal medulla. The data may be specific to the patient into which the device is implanted, and gleaned from various tests known in the art. Upon receipt of signals received from the one or more sensors, or else periodically or upon demand, the processor may compare the signals received from the one or more sensors with the physiological data stored in the memory and determine whether the received signals are indicative of insufficient or excessive levels of signaling molecules secreted from the adrenal medulla. The device may be configured such that if and when an insufficient or excessive level of signaling molecules secreted from the adrenal medulla is indicated, the processor triggers delivery of a signal to a branch of the GSN supplying the adrenal gland by the at least one transducer, in the manner described elsewhere herein. For instance, if a signal indicative of insufficient Epi, NE or enkephalin concentration in the circulation is detected, the processor may trigger delivery of a signal which increases secretion of the respective signaling molecule, as described elsewhere herein. If a signal indicative of excessive Epi, NE or enkephalin concentration in the circulation is detected, the processor may trigger delivery of a signal which dampens secretion of the respective signaling molecule, as described elsewhere herein.

As an alternative, or in addition, to the device's ability to respond to sensed physiological signals, the processor may be triggered upon receipt of a signal generated by a physician or by the subject in which the device is implanted. To that end, the implantable device may be part of a system comprising subsystems external to the subject, and including, for instance, a controller. An example of such a system is described below.

The controller may be configured to apply any one or more of the above signals to a branch of the GSN supplying the adrenal gland intermittently or continuously. Intermittent application of a signal involves applying the signal in an (on-off)$_n$ pattern, where n>1. For instance, the signal can be applied continuously for at least 5 days, optionally at least 7 days, before ceasing for a period (e.g. 1 day, 2 days, 3 days, 1 week, 2 weeks, 1 month), before being again applied continuously for at least 5 days, etc. Thus the signal is applied for a first time period, then stopped for a second time period, then reapplied for a third time period, then stopped for a fourth time period, etc. In such an embodiment, the first, second, third and fourth periods run sequentially and consecutively. The duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d.

In certain embodiments, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

Continuous application may continue indefinitely, e.g. permanently. Alternatively, the continuous application may be for a minimum period, for example the signal may be continuously applied for at least 5 days, or at least 7 days.

Where the signal is controlled by a device/system of the invention, and where a signal is continuously applied to the nerve, although the signal might be a series of pulses, the gaps between those pulses do not mean the signal is not continuously applied.

In certain embodiments, the signal is applied only when the subject is in a specific state e.g. only when the subject is awake, only when the subject is asleep, prior to and/or after the ingestion of food, prior to and/or after the subject undertakes exercise, etc.

These various embodiments for timing of inhibition can all be achieved using the controller in a device/system of the invention.

Other Components of the Implantable Device

The implantable device may be powered by a power source, which may comprise a current source and/or a voltage source for providing the power for the signal delivered to a branch of the GSN supplying the adrenal gland by the at least one transducer. The power source may also provide power for the other components of the device, such as the microprocessor, memory and communication subsystem (described below). The power source may comprise a battery and may be rechargeable. It will be appreciated that the availability of power is limited in implantable devices, and the invention has been devised with this constraint in mind. The device/system may be powered by inductive powering or a rechargeable power source.

The implantable device may comprise a communication subsystem, for instance comprising a transceiver coupled to the processor. The transceiver may use any suitable signaling process such as RF, wireless, infrared and so on, for transmitting signals outside of the body, for instance to a system of which the implantable device is one part.

System Including Implantable Device

The implantable device of the invention may be part of a system that includes a number of subsystems. For instance, the system may comprise subsystems located outside of the body, including a subsystem for wirelessly recharging the battery used to power the implantable device, and a controller with a communications subsystem that is configured to communicate with the communications subsystem of the implantable device.

The controller may comprise an actuator which, upon being pressed by a physician or the subject for instance, will deliver a signal, via the respective communications subsystems, to trigger the processor of the implantable device to deliver a signal to a branch of the GSN supplying the adrenal gland by the at least one transducer.

The controller may also be configured to make adjustments to the operation of the implantable device. For instance, it may transmit, via the respective communications subsystems, physiological data pertaining to a normal level of signaling molecules secreted from the adrenal medulla. The data may be specific to the patient into which the device is implanted. The controller may also be configured to make adjustments to the operation of the power source, signal generation and processing elements and/or electrodes in order to tune the signal current delivered to a branch of the GSN supplying the adrenal gland by each node of an electrode, or by each electrode.

A device/system of the invention is preferably made from, or coated with, a biostable and biocompatible material. This means that the device/system is both protected from damage due to exposure to the body's tissues and also minimises the risk that the device/system elicits an unfavourable reaction by the host (which could ultimately lead to rejection). The material used to make or coat the device/system should ideally resist the formation of biofilms. Suitable materials include, but are not limited to, poly(p-xylylene) polymers (known as Parylenes) and polytetrafluoroethylene.

A device/system of the invention will generally weigh less than 50 g.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x+10%.

Unless otherwise indicated each embodiment as described herein may be combined with another embodiment as described herein.

BRIEF DESCRIPTION OF THE DRAWINGS

FIGS. 2(Di) and (Dii) show further example voltammograms for TBS supplemented with NE and Epi, respectively, over a range of concentrations relevant to the biological context. (Di) A single primary ("1st") oxidation current peak is observed for NE. (Dii) The graph displays both a primary ("1st") and a secondary ("2nd") oxidation peak current characteristic of Epi. (E) A graph showing the magnitude of the first peak in the NE calibration voltammogram in (Di) relative to the NE concentration. (F) A graph showing the magnitudes of the first peak and second peak in the Epi calibration voltammogram in (Dii) relative to the Epi concentration. The ratio of the magnitude of the second peak to the first peak is used to assign relative release of Epi to NE as described in the text.

Figure 2:
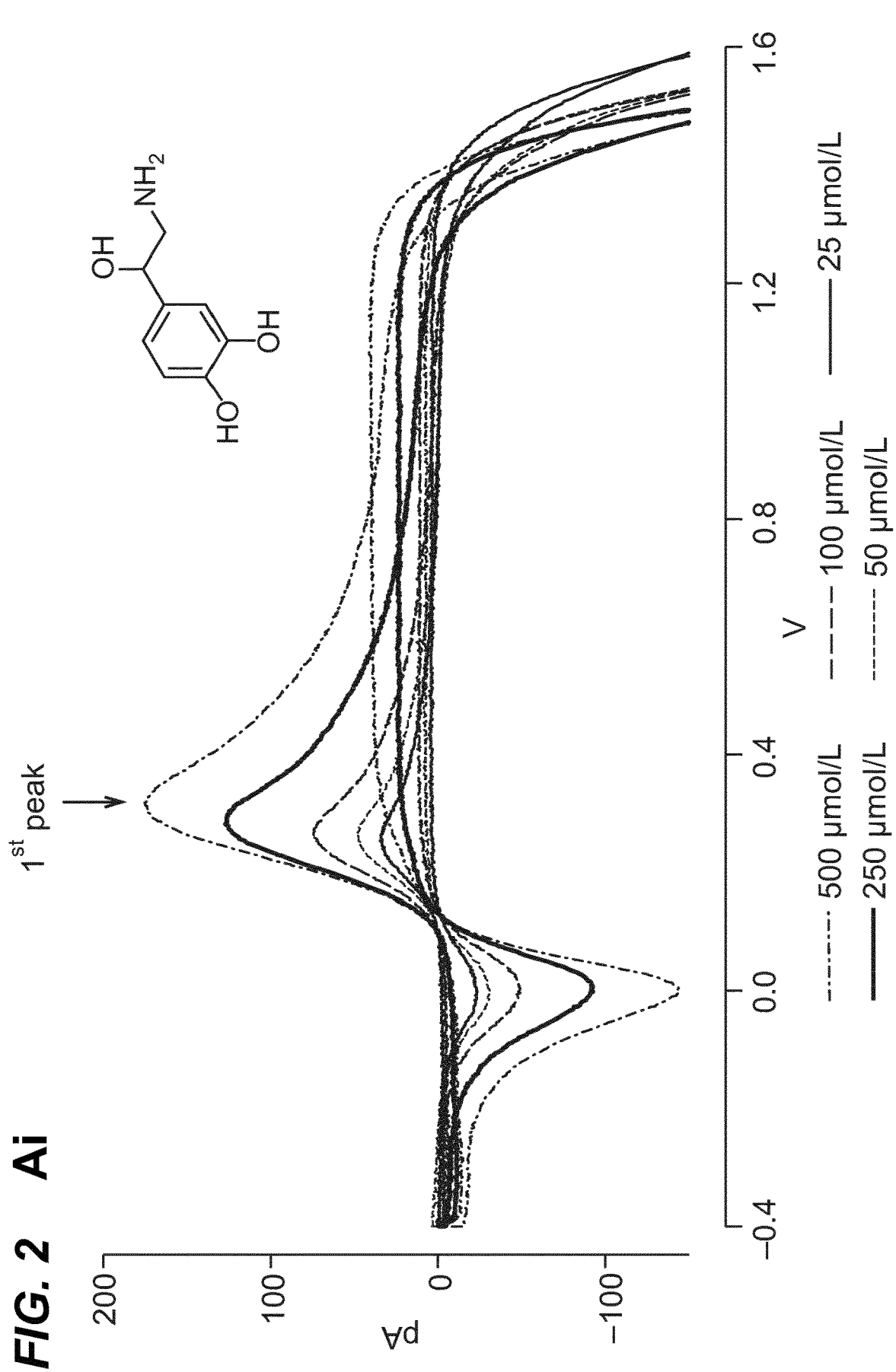
FIG. 2. Current-based calibration of the FSCV voltammograms. (Ai) Voltammograms were recorded and background subtracted as described in FIG. 1. Panel Ai shows such example voltammograms for TBS supplemented with norepinephrine (NE) over a range of concentrations relevant to the biological context. A single primary ("1st") oxidation current peak is observed for NE. (Aii) An equivalent set of FSCV voltammograms is provided for Epi-supplemented TBS and display both a primary ("1st") and a secondary ("2nd") oxidation peak current. The second peak is diagnostic for Epi. (B) The magnitude of the first peak in the NE calibration voltammogram set in (Ai) follows an exponential function depending on NE concentration. (C) Both the primary and secondary oxidation peaks for Epi in (Aii) follow exponential dependences on concentration. (Inset) The ratio of the magnitude of the second peak to the first peak in the Epi voltammogram follows an exponential function (reaction constant=0.009 μM−1) and may be used to assign relative release of Epi to NE as described in the text.
Figure 2:
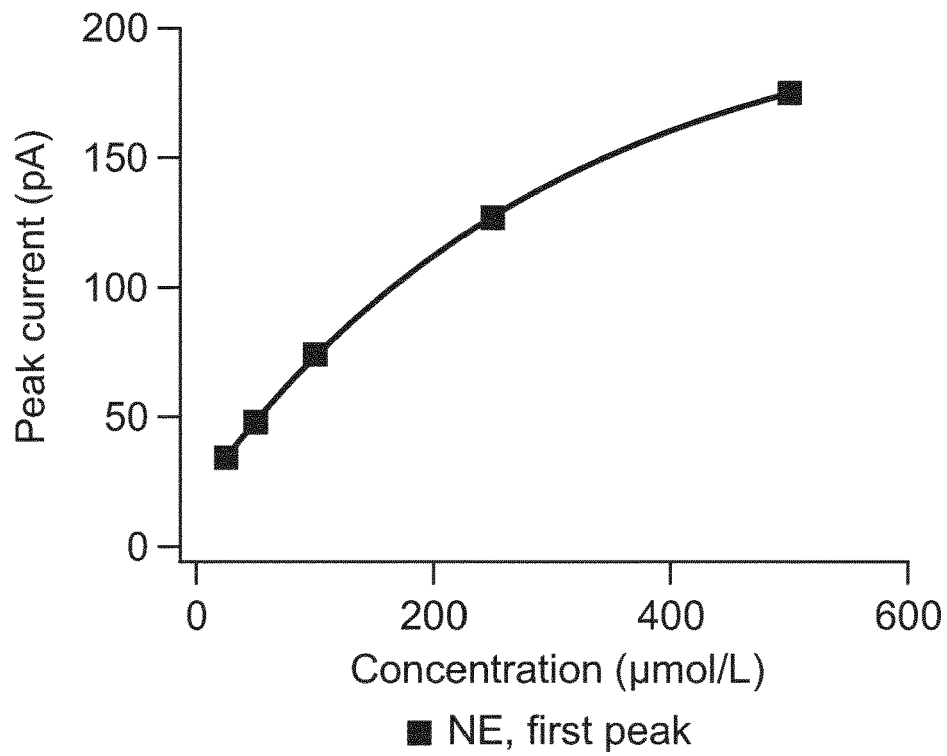
Figure 2:
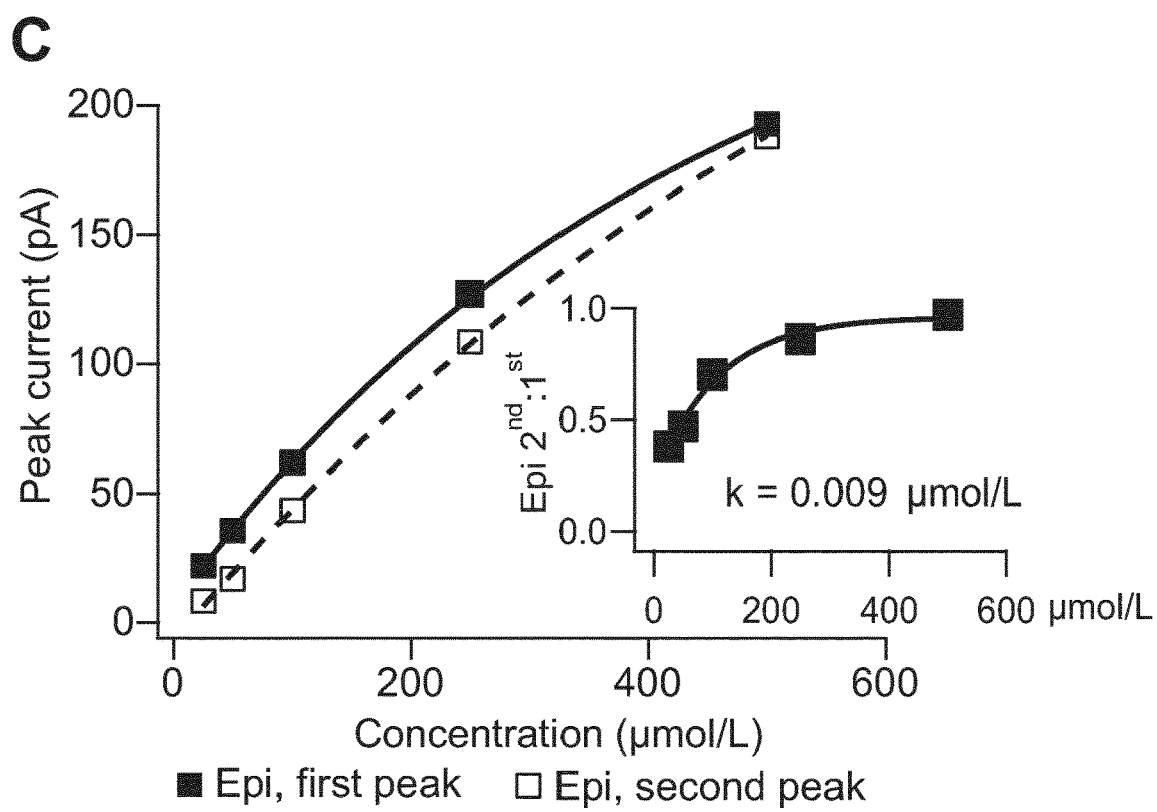
Figure 2:
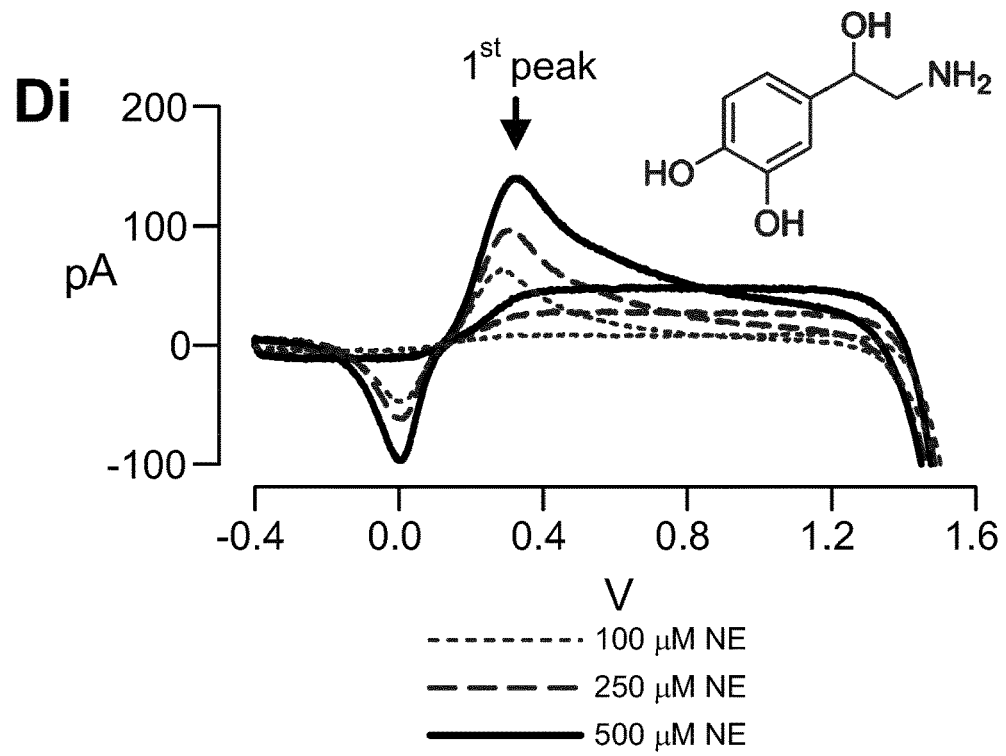
Figure 2:
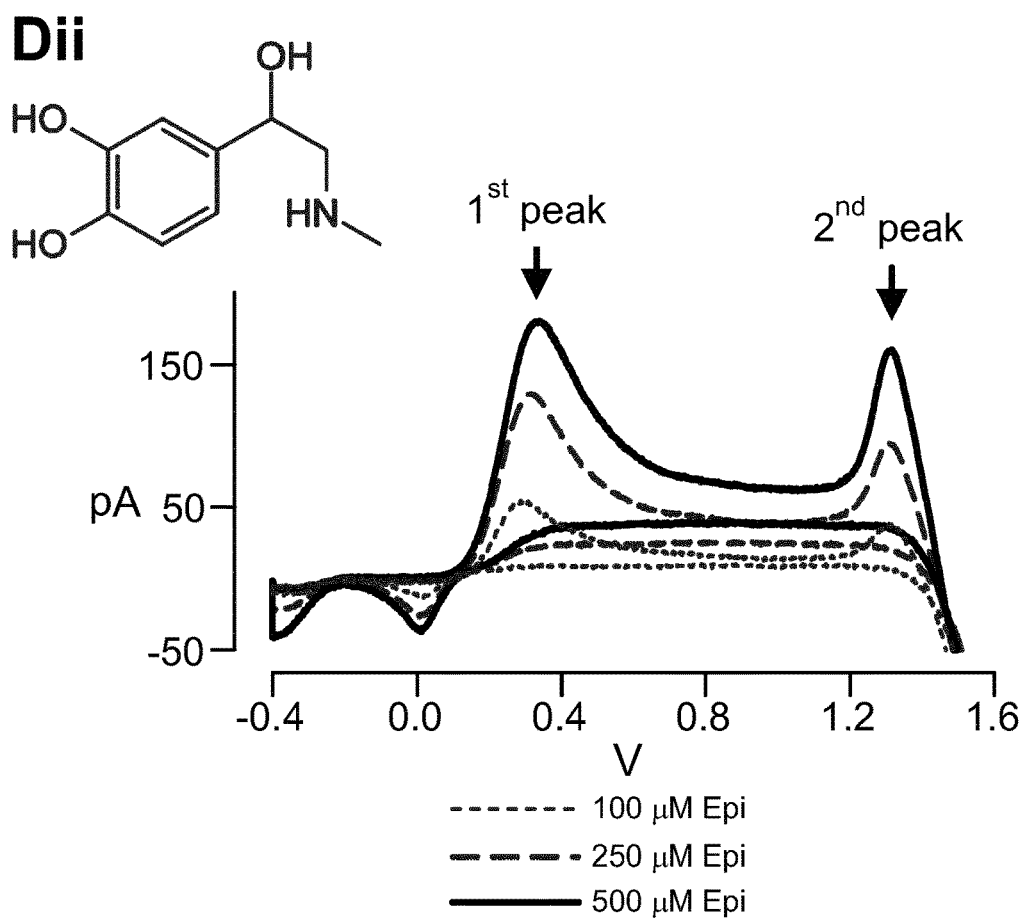
Figure 2:
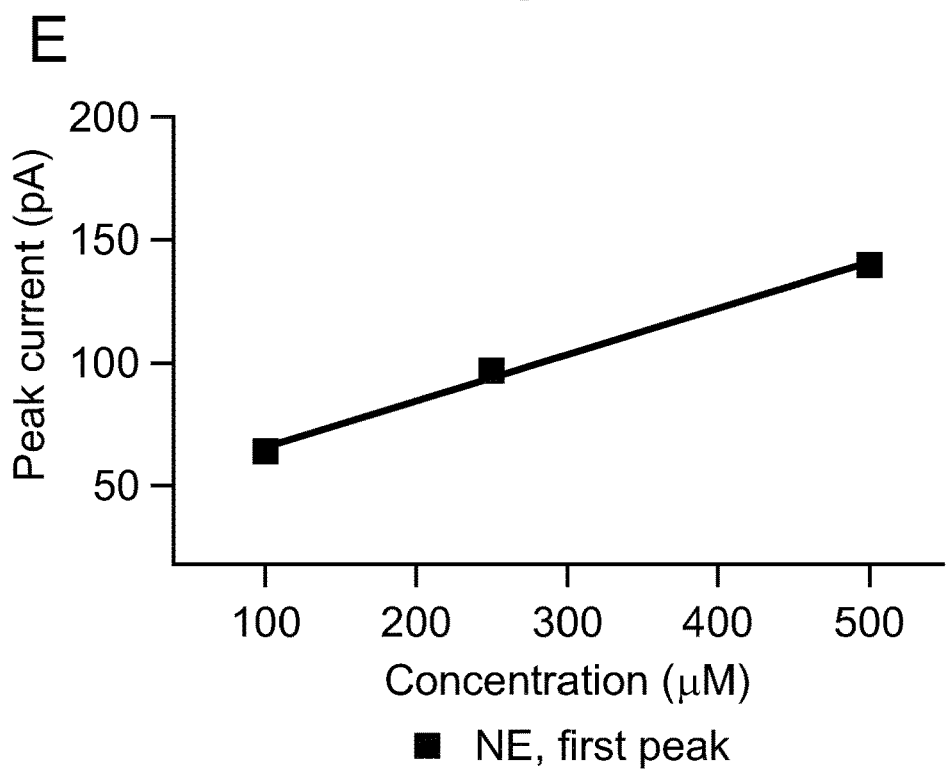
Figure 2:
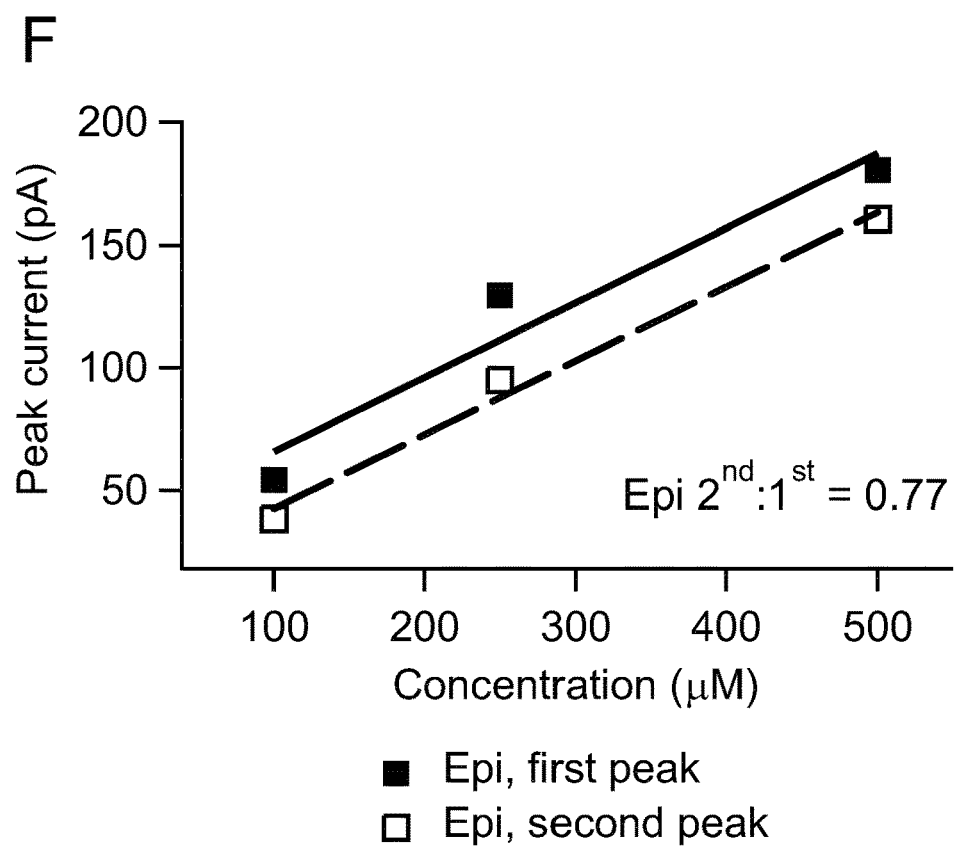

(Di) The potential at which the primary oxidation reaches its peak amplitude follows a linear function (stippled line across all peaks) dependent on the concentration of NE in the bath and represents an independent second calibration parameter to complement the current-based approach presented in FIG. 2. (Dii) The same concentration-dependent linear dependence on concentration observed in the NE context is also present in the primary oxidation signal for Epi (stippled line across all first peaks). No such concentration dependence is observed in the secondary oxidation signal (stippled line across all second peaks). (E) The concentration dependence of the potential at which the primary oxidation current reaches its peak amplitude in (Di) and (Dii) is presented for both the NE (■, solid line) and Epi (□, stippled line). (F) The potential at which the secondary oxidation peak is reached for Epi is constant at 1.31 V.

Figure 4:
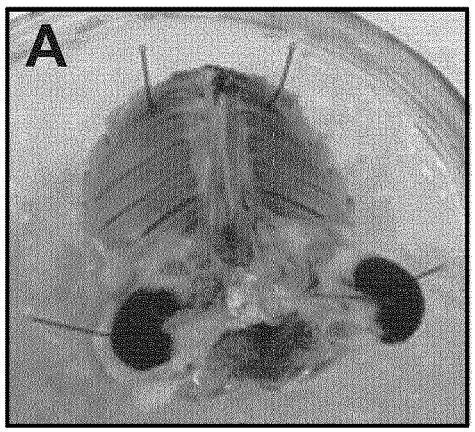
Figure 4:
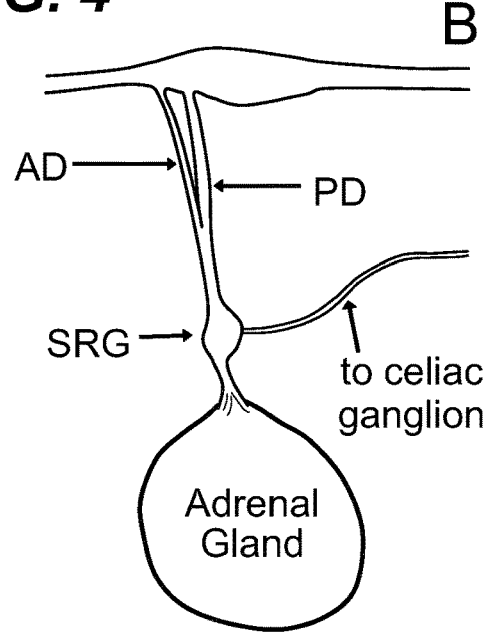
Figure 4:
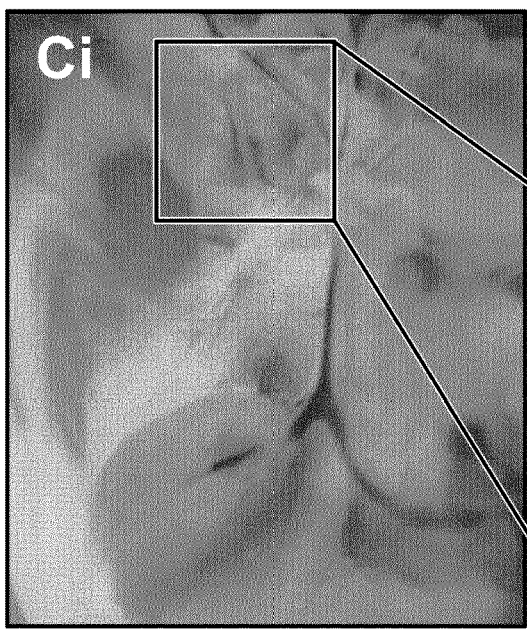
Figure 4:
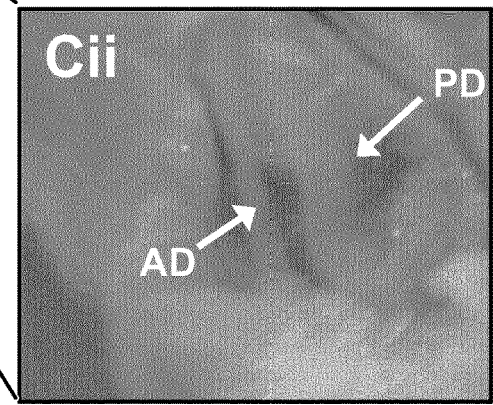
Figure 4:
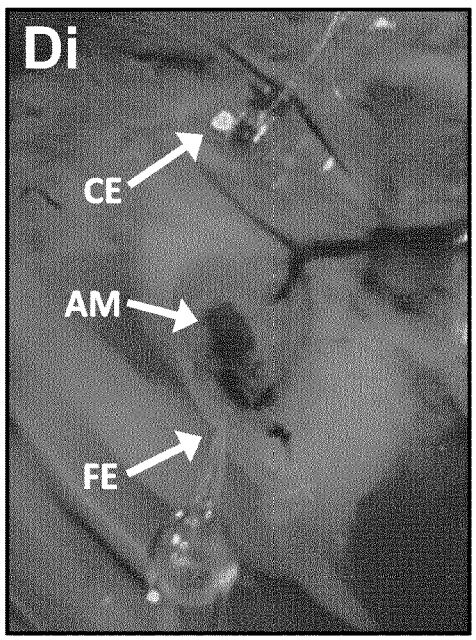
Figure 4:
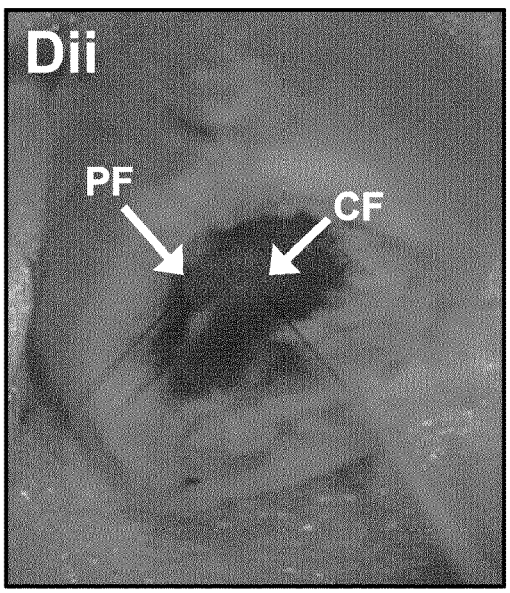

FIG. 4. An Ex Vivo spinal-splanchnic-adrenal preparation. (A) Ventral view of the posterior wall of a rat is isolated between approximately T1 and L5 vertebrae. The preparation includes the entire splanchnic nerve as it innervates the adrenal gland. Scale=10 mm. (B) A cartoon representation is provided for clarity in identifying relevant features in the ex vivo preparation. (Ci) An image similar to the cartoon representation in B is provided showing the gland in the lower region as well as the innervating splanchnic descending to the gland. Scale=5 mm. (Cii) The inset box in Ci is blown up to show both the anterior division (AD) and posterior division (PD) of the splanchnic nerve as it innervates the adrenal gland. (Di) A cuff electrode (CE) is placed on the splanchnic nerve. The gland is hemisected to expose the medulla (AM) and an FSCV carbon fibre electrode (FE) is positioned to measure catecholamine at the exposed medulla. Scale=5 mm. (Dii) A close up image of the hemisected gland shows the exposed medullary tissue which is darker in appearance. Two carbon fibre electrodes (peripheral fibre "PF" and central fibre "CF") can be seen in the image. Scale=1 mm.

Figure 3:
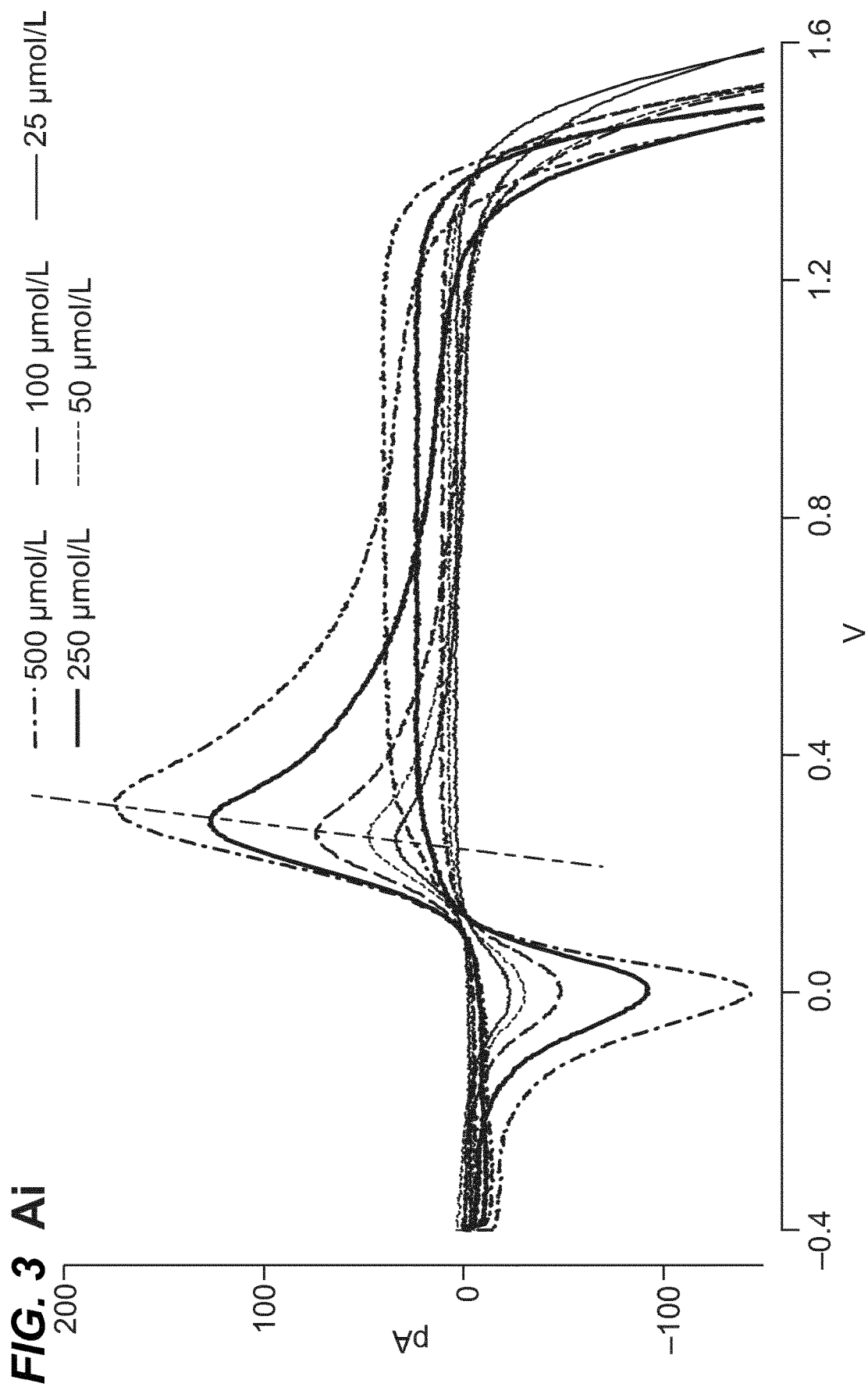
FIG. 3. Voltage-based calibration of the FSCV voltammograms. (Ai) The potential at which the primary oxidation reaches its peak amplitude follows a linear function (stippled line across all peaks) dependent on the concentration of NE in the bath and represents an independent second calibration parameter to complement the current-based approach presented in FIG. 2. (Aii) The same concentration-dependent linear dependence on concentration observed in the NE context is also present in the primary oxidation signal for Epi (stippled line across all first peaks). No such concentration dependence is observed in the secondary oxidation signal (stippled line across all second peaks). (B) The concentration dependence of the potential at which the primary oxidation current reaches its peak amplitude in (Ai) and (Aii) is presented for both the NE (■, solid line) and Epi (□, stippled line). (C) The potential at which the secondary oxidation peak is reached for Epi is relatively flat at 1.30 V.
Figure 3:
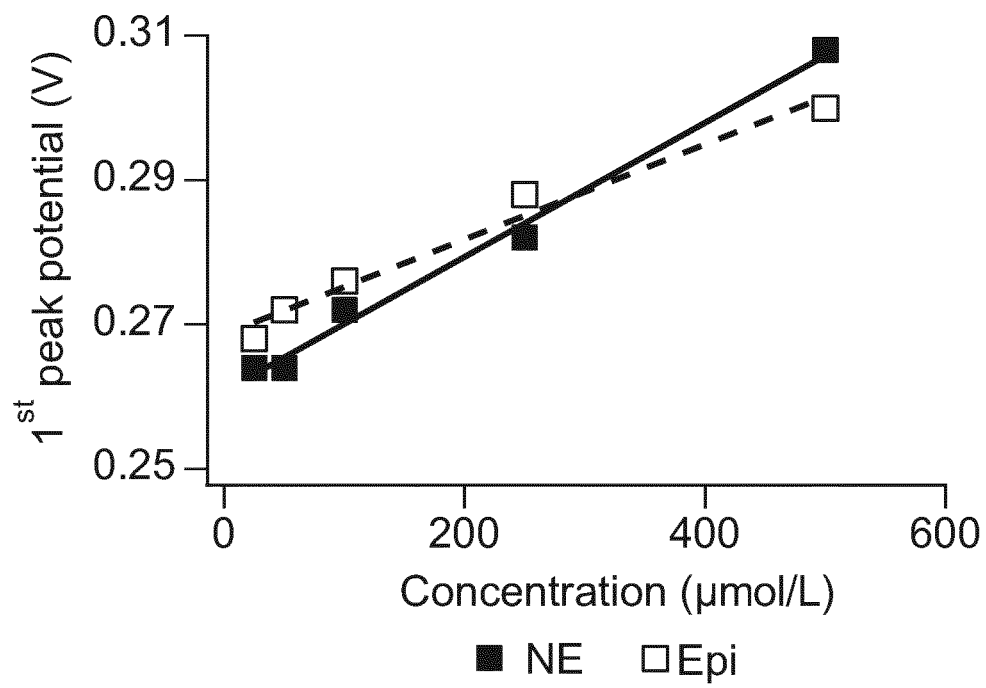
Figure 3:
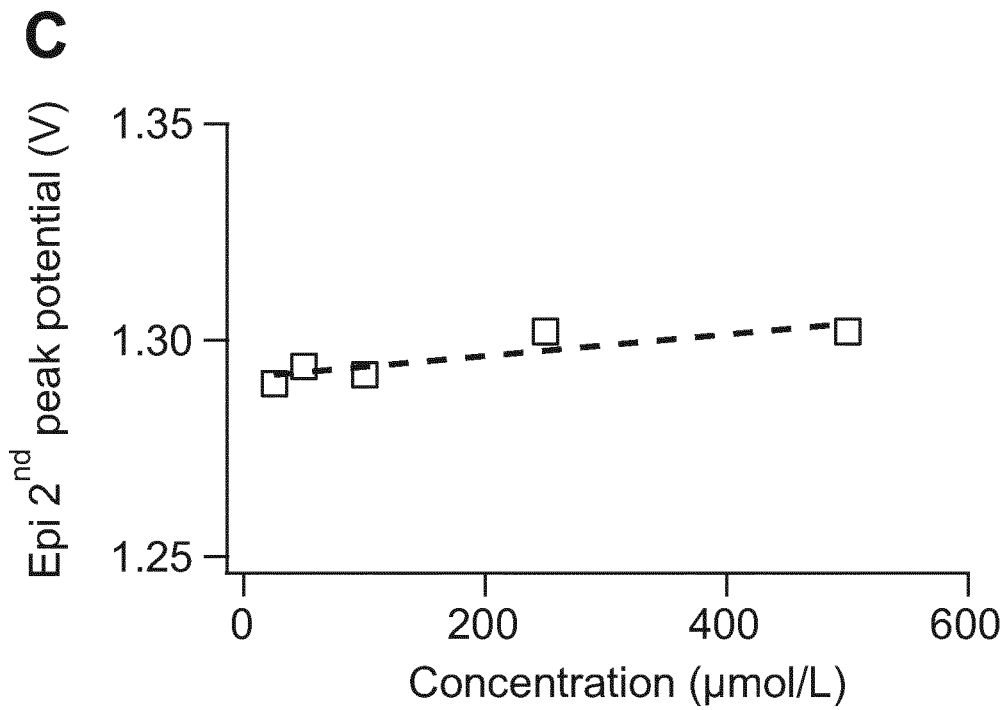
Figure 3:
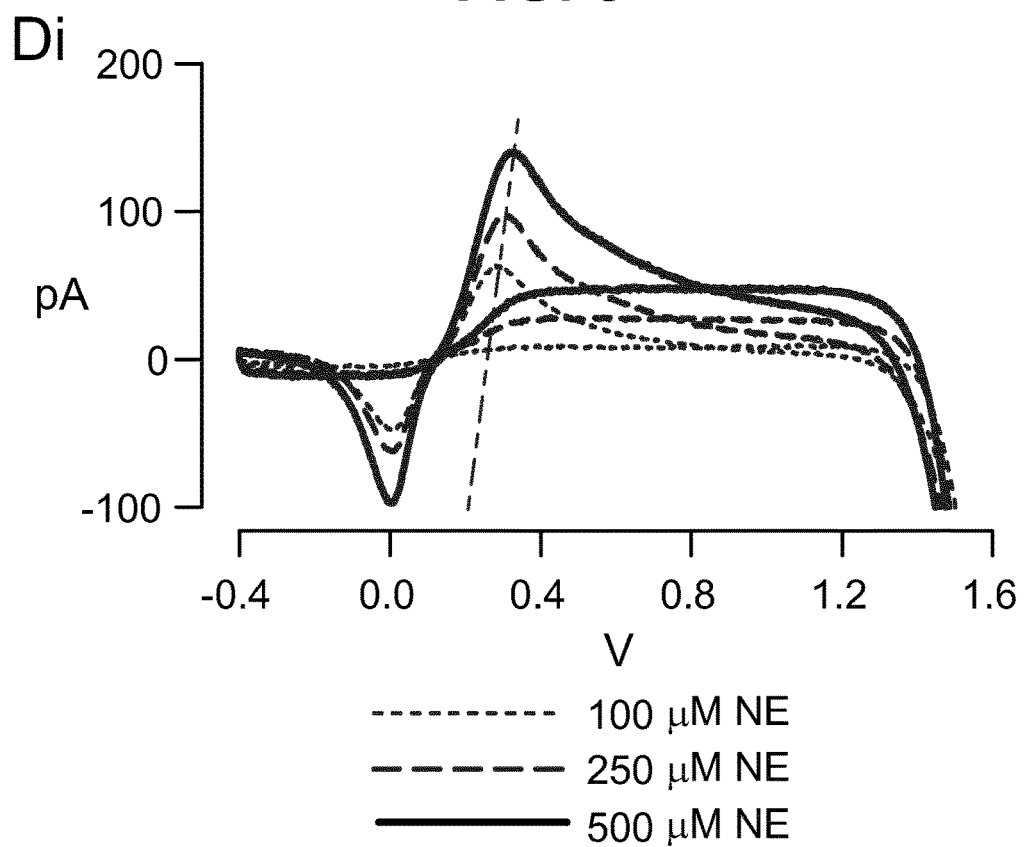
Figure 3:
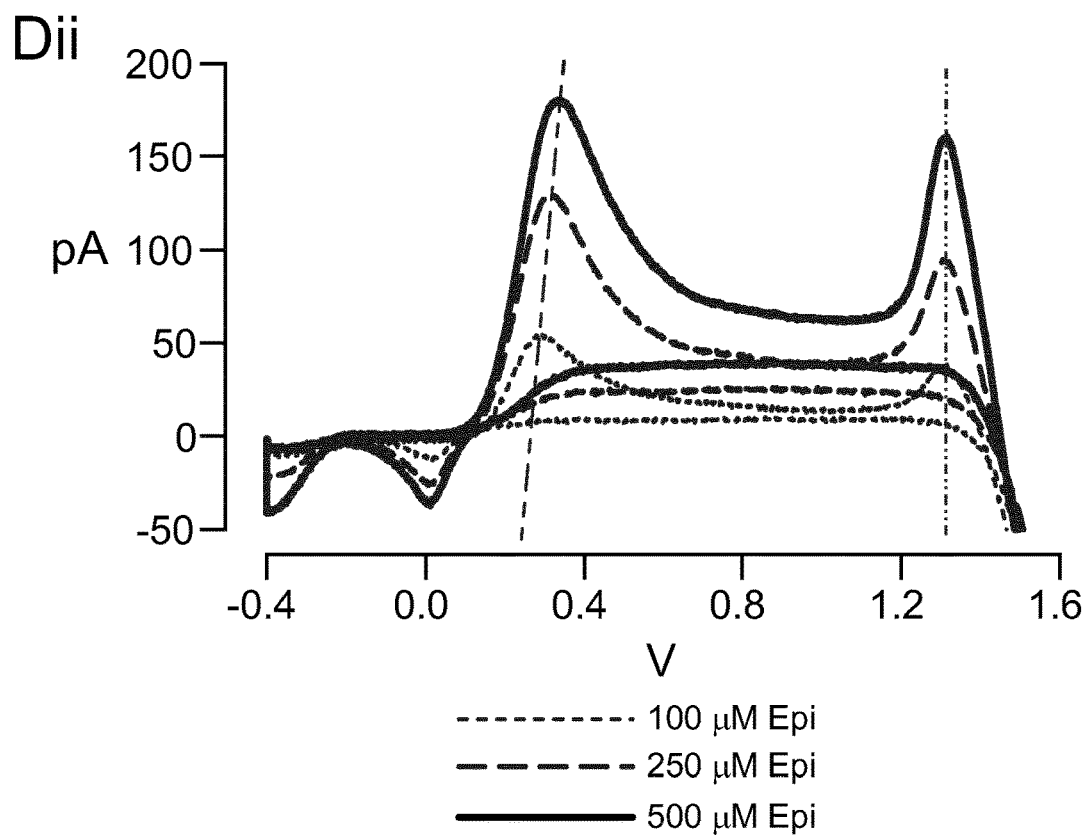
Figure 3:
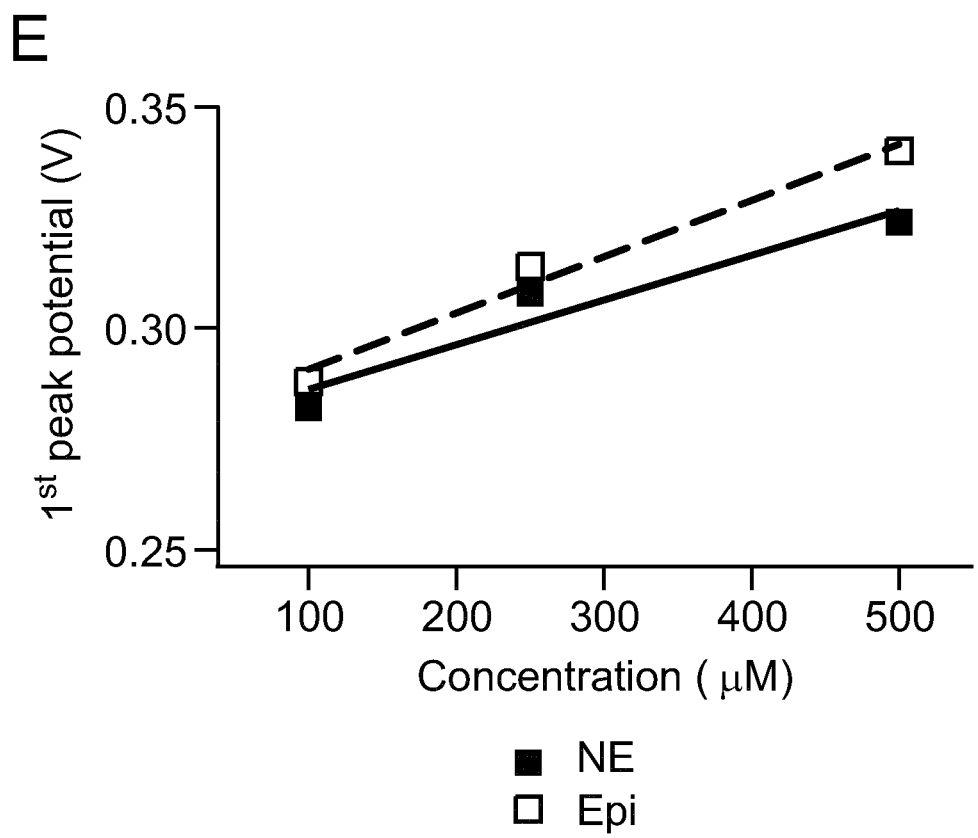
Figure 3:
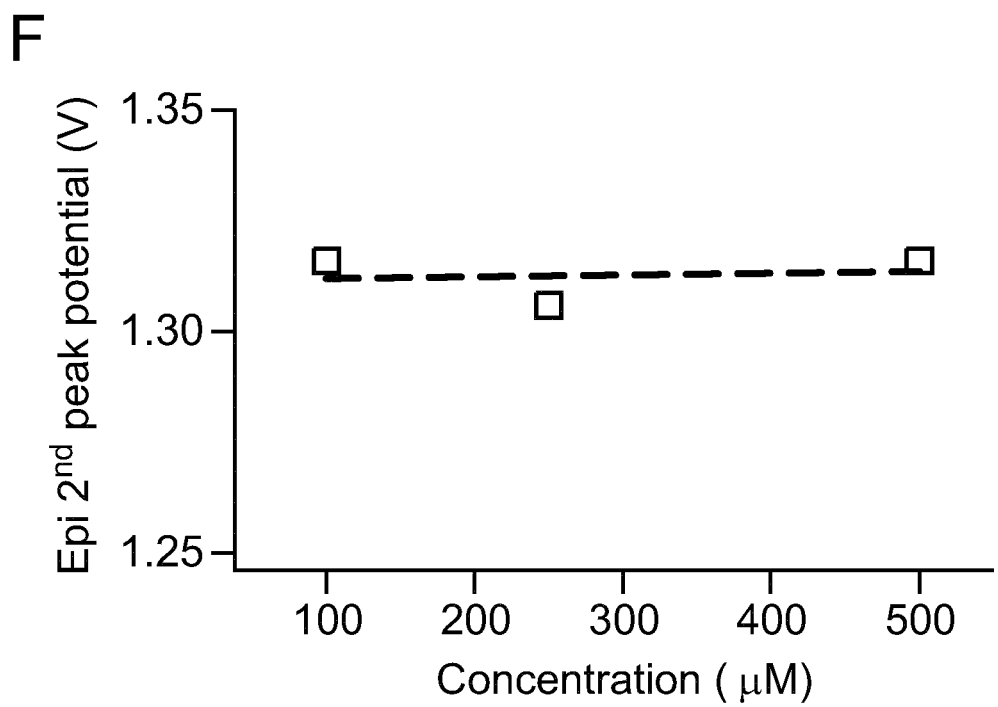
Figure 5:
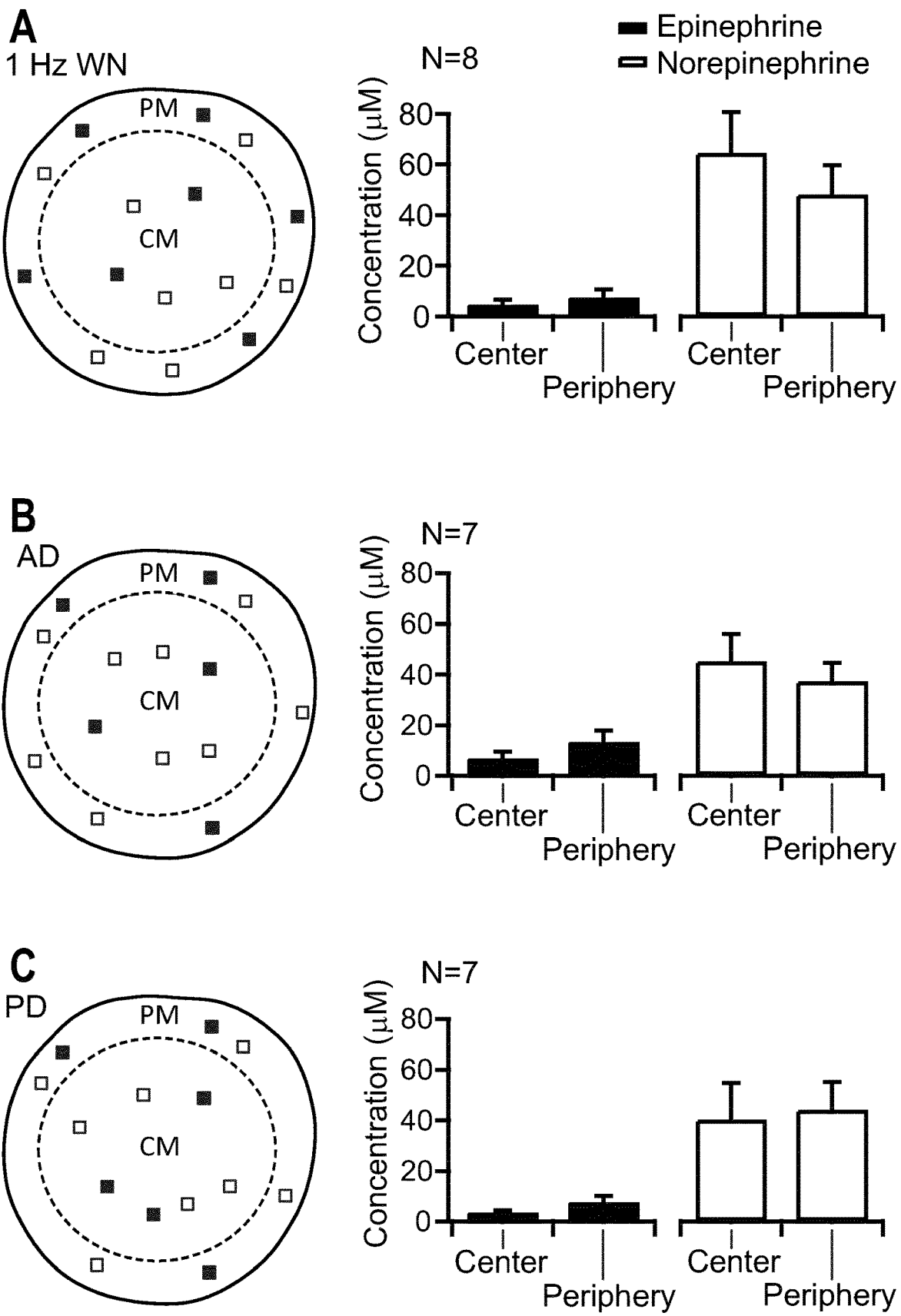

FIG. 5. Epinephrine and norepinephrine release at 1 Hz nerve stimulation. (Left column) Cartoon representations for the hemisected adrenal medullary face are provided. Each map is further divided into peripheral medulla (PM) and central medulla (CM) by a dotted line. Symbols demonstrate whether signal for either Epi (■) or NE (□) were detected in the gland periphery or centre. It should be noted that detection of both Epi and NE would provide a symbol for both. The top cartoon represents results when the whole nerve ("WN") was stimulated. Below are representations for both anterior division ("AD") and posterior division ("PD") stimulation conditions. (Right column) Epi or NE signals were calibrated as demonstrated in FIGS. 2 and 3 and are provided for each condition. Numbers of recordings in each data set are provided in the upper left of each category plot. Data are supplied as mean±SEM.

Figure 6:
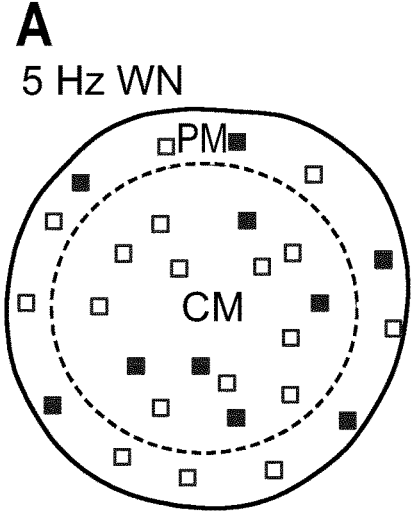
Figure 6:
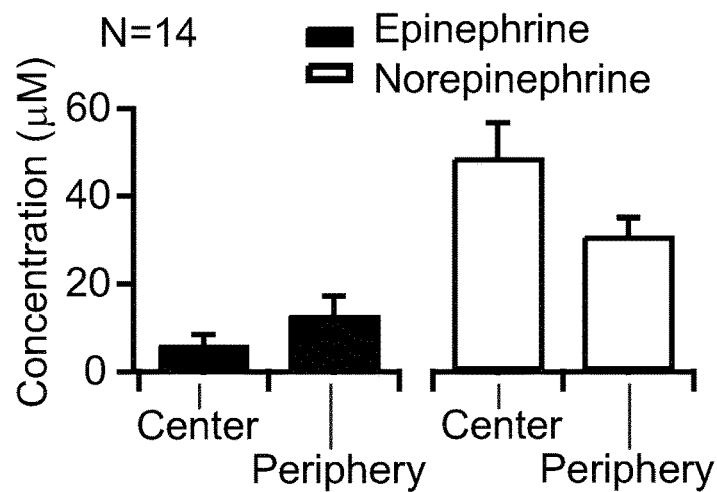
Figure 6:
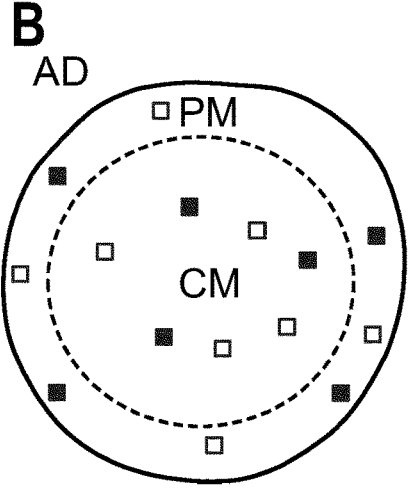
Figure 6:
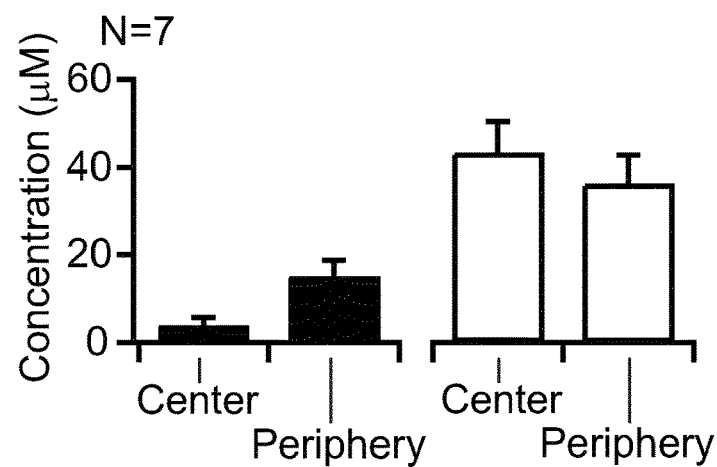
Figure 6:
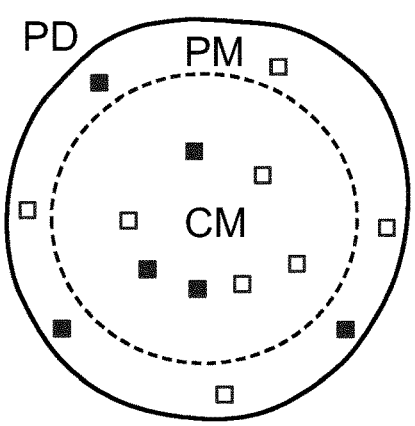
Figure 6:
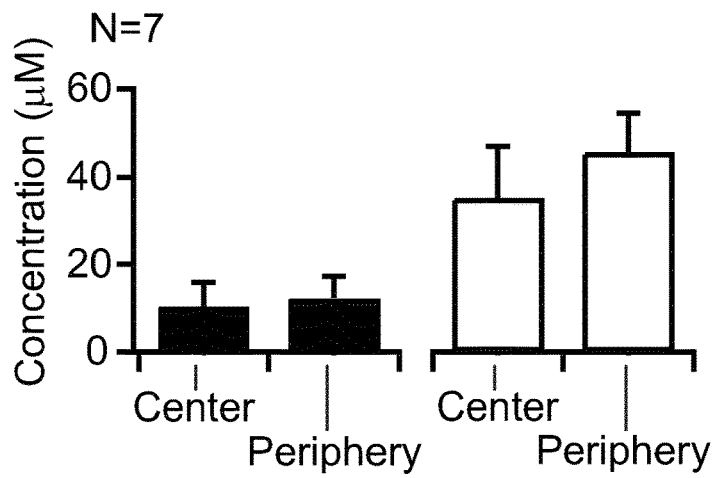

FIG. 6. Epinephrine and norepinephrine release at 5 Hz nerve stimulation. (Left column) Cartoon representations equivalent to those in FIG. 5 are provided, except that they represent the 5 Hz stimulation condition. Symbols demonstrate whether signal for either Epi (■) or NE (□) were detected in the gland periphery or centre. It should be noted that a mixed signal would provide a symbol for both Epi and NE. The top cartoon represents results when the whole nerve ("WN") was stimulated. Below are representations for both anterior division ("AD") and posterior division ("PD") stimulation conditions. (Right column) Epi or NE signals were calibrated as demonstrated in FIGS. 2 and 3 and are provided for each condition. Numbers of recordings in each data set are provided in the upper left of each category plot.

Figure 7:
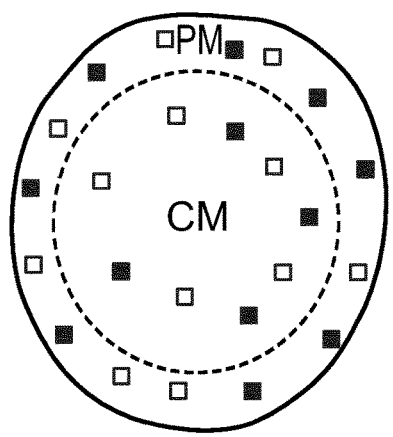
Figure 7:
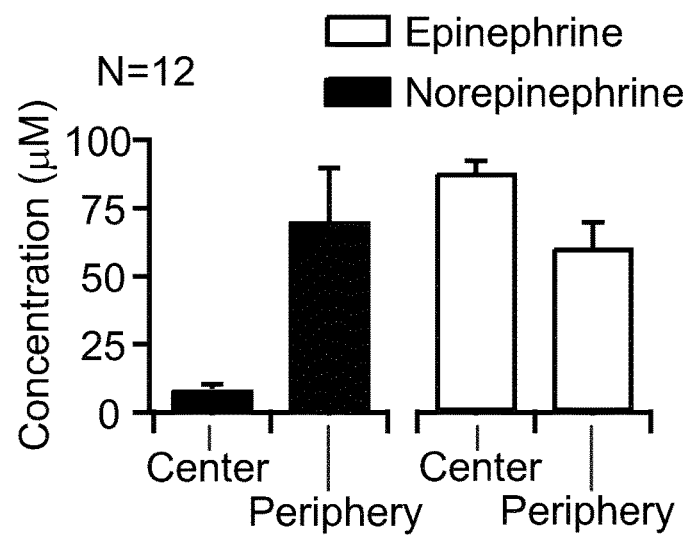
Figure 7:
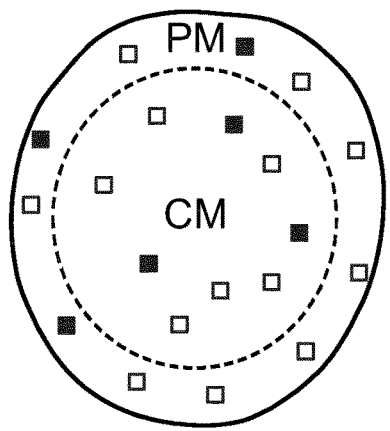
Figure 7:
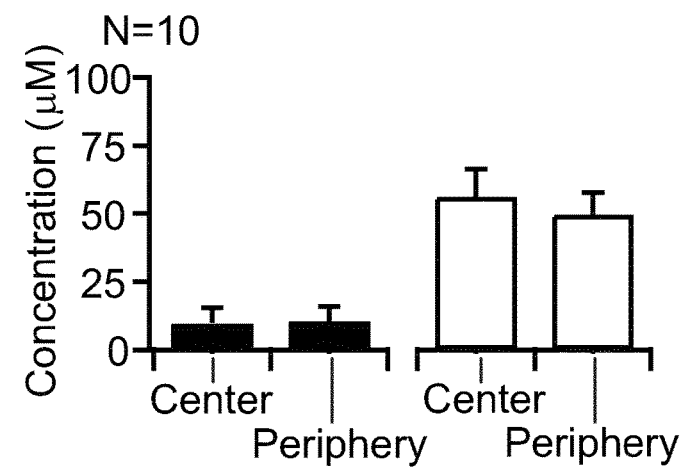
Figure 7:
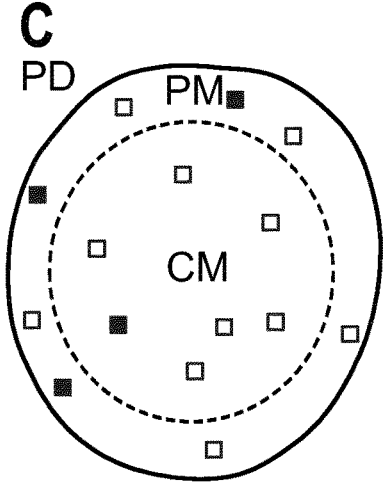
Figure 7:
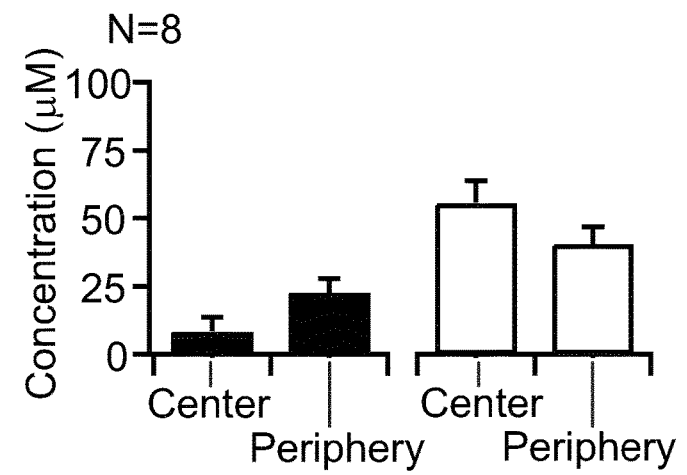

FIG. 7. Epinephrine and norepinephrine release at 10 Hz nerve stimulation. (Left column) Cartoon representations equivalent to those in FIG. 5 are provided, except that they represent the 10 Hz stimulation condition. Symbols demonstrate whether signal for either Epi (■) or NE (□) were detected in the gland periphery or centre. It should be noted that a mixed signal would provide a symbol for both Epi and NE. The top cartoon represents results when the whole nerve ("WN") was stimulated. Below are representations for both anterior division ("AD") and posterior division ("PD") stimulation conditions. (Right column) Epi or NE signals were calibrated as demonstrated in FIGS. 2 and 3 and are provided for each condition. Numbers of recordings in each data set are provided in the upper left of each category plot.

Figure 8:
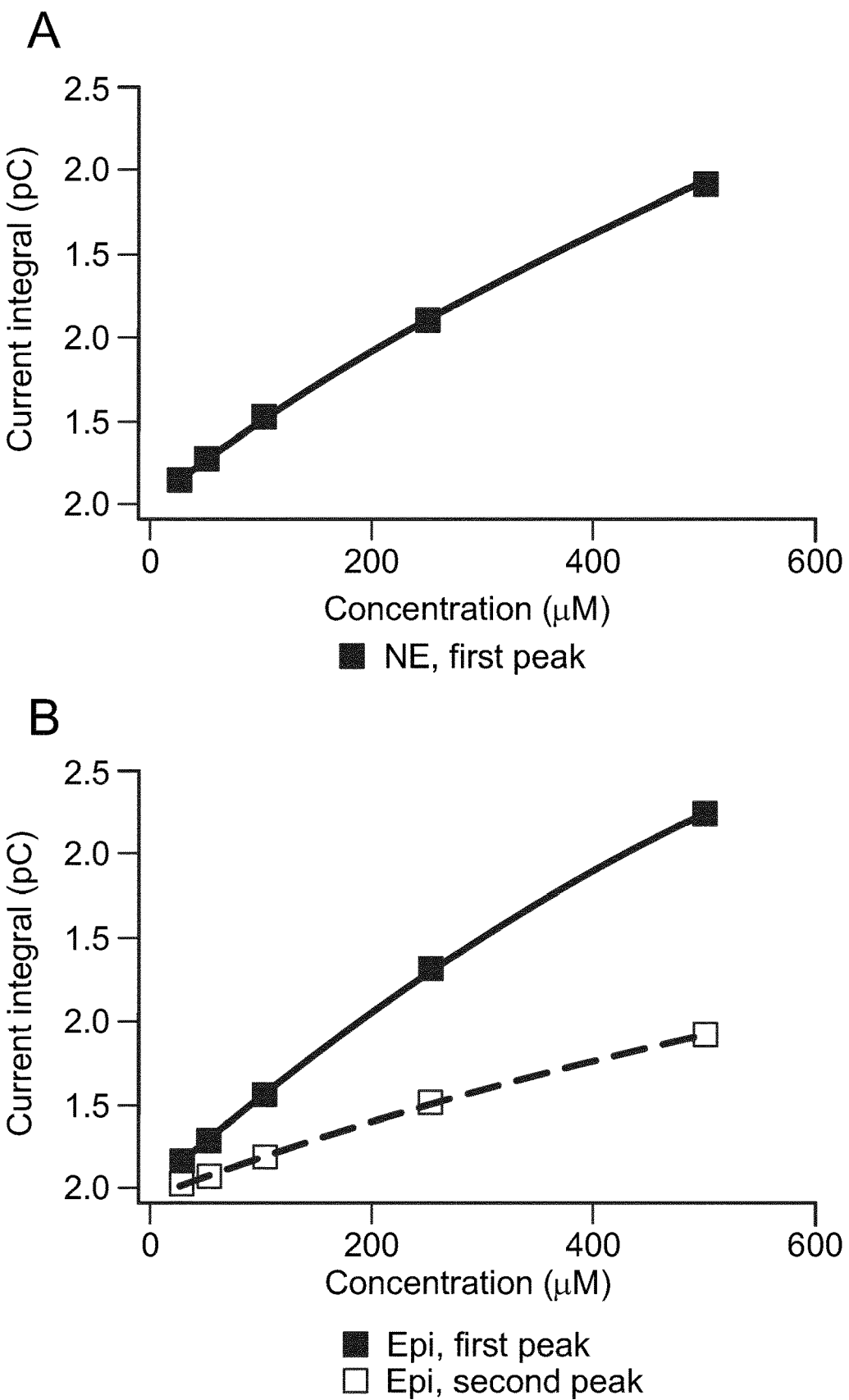

FIG. 8. In vitro calibration measured as integrated current. Voltammograms were measured in standard concentrations of either norepinephrine (NE) or epinephrine (Epi), background subtracted and plotted as described in the text for FIG. 2. Catecholamine specific currents were integrated to provide total detected charge and are plotted against catecholamine concentration. (A) The integral of the first peak in the NE calibration voltammogram set follows an exponential function depending on NE concentration. (B) Both the primary and secondary oxidation current integrals for Epi follow exponential dependences on concentration as well.

Figure 9:
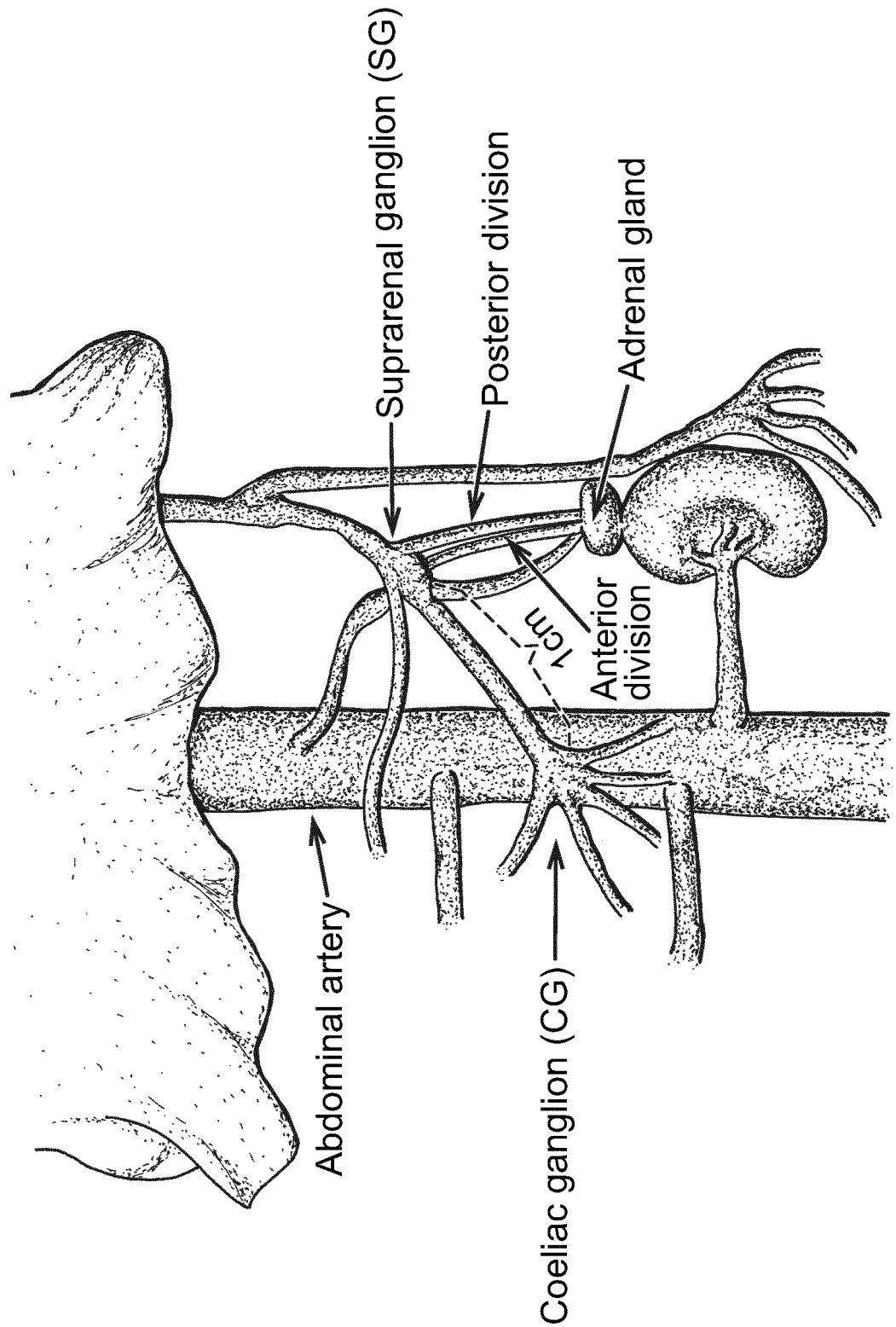

FIG. 9 is a schematic diagram depicting the gross anatomic arrangement of the adrenal innervation. The adrenal glands, abdominal artery, celiac ganglion, suprarenal ganglion, and the posterior and anterior divisions of the branch of the GSN supplying the adrenal gland between the suprarenal ganglion and the adrenal gland are labelled.

MODES FOR CARRYING OUT THE INVENTION

Early studies of the sympatho-adrenal stress response demonstrated a stressor-dependent preferential release of epinephrine or norepinephrine from the adrenal medulla to initiate the appropriate physiological response to the given stressor (Coupland, 1958; Klevans & Gebber, 1970; Vollmer et al., 1992; Vollmer, 1996; Goldstein, 2010; Kvetnansky et al., 2013). The splanchnic nerve bifurcates into two divisions, anterior and posterior divisions, before innervating the adrenal gland (Celler & Schramm, 1981). There is also evidence for the differential innervation of epinephrine and norepinephrine-secreting cell types by histologically and electrophysiologically distinguishable nerve fibres (Edwards et al., 1996; Cao & Morrison, 2001), raising the intriguing hypothesis that either division of the splanchnic represents specific innervation of either epinephrine- or norepinephrine-secreting chromaffin cells.

We addressed this hypothesis in a novel rat ex vivo splanchnic-adrenal experimental system. The innervating splanchnic nerve was stimulated to evoke catecholamine release from a hemisected adrenal gland. We then utilized fast scanning cyclic voltammetry (FSCV) (Kawagoe et al., 1991; Leszczyszyn et al., 1991) to identify and measure evoked epinephrine and norepinephrine release. Next, we generated a spatial map of epinephrine and norepinephrine release from the adrenal medulla under varied neuronal stimulation frequencies. Lastly, we tested the activity of both branches of the splanchnic to control either epinephrine or norepinephrine.

Materials and Methods

Ethical Approval:

Animal care and use was in accordance with National Institutes of the Health and Case Western Reserve University institutional guidelines (United States Federal welfare assurance number #A3145-01). All protocols were approved by the Institutional Animal Care and Usage Committee (IACUC) and are in accordance with the 2013 American Veterinary Medical Association guidelines for animal euthanasia.

Chemicals:

All chemicals were purchased from Sigma-Aldrich (St. Louis, Mo., USA) and used as received unless otherwise specified. Epinephrine was obtained as L(-)Epinephrine from MP Biomedicals, LLC (Solon, Ohio, USA). Electrochemical and ex-vivo experiments were carried out in Tris (tris(hydroxymethyl) aminomethane) buffered saline (TBS; 132 mM NaCl, 40 mM Tris, 11.2 mM Glucose, 4.2 mM KCl, 2 mM CaCl2, 0.7 mM MgCl2) at pH 7.4. In vitro FSCV control experiments were conducted in TBS with epinephrine (Epi) or norepinephrine (NE) added as indicated in the text. All solutions were made from double deionized water >17.5 MΩ·cm.

Ex Vivo Preparation:

Sprague-Dawley rats (225-275 g, Charles River Laboratories, Raleigh, N.C., USA) were housed in the Animal Resource Center of Case Western Reserve University and were provided with food and water ad libitum. For tissue harvest, rats were deeply anesthetized with isoflurane and euthanized by decapitation and bilateral pneumothorax. Anaesthesia was determined by monitoring the rat until completely unresponsive and breathing ceased. The peritoneum was opened and superfused with an ice-cold low-calcium physiological saline of the following composition (in mM): 150 NaCl, 10 HEPES-H, 10 Glucose, 2.8 KCl, 4.3 $MgCl_2$, 0.5 $CaCl_2$, pH to 7.2. The back wall of the peritoneum was rapidly dissected and isolated. This section of the wall extends between approximately vertebrae T1 and L5 and extends laterally to include the kidneys and adrenal glands. While all the viscera in the peritoneal cavity were removed, the kidneys and adrenal glands, and their associated vessels and nervous tissue in the retroperitoneal region, were preserved. The preparation was pinned out on a silicone elastomer substrate and the bath solution changed to a TRIS-buffered saline (TBS) as described above. All recordings were performed at 23-25° C. and within 1 hour after animal termination.

Most rats presented a readily-observable discrete bifurcation in the splanchnic nerve between sympathetic chain ganglion and the innervation of the adrenal gland. Previous anatomical studies of the rat splanchnic described heterogeneity where approximately 30% of rats did not exhibit two divisions in the splanchnic (Celler & Schramm, 1981). We did not find this heterogeneity, but on occasion (approximately 15-20% of rats, by empirical observations), the divisions of the splanchnic were closely associated and not readily separable without damaging the nerves. In these instances, the animal was used for whole nerve recording only. Before recording, the adrenal gland was hemisected to expose the adrenal medulla. One carbon fibre electrode was then placed at the periphery of the adrenal medulla, while another was placed in the centre of the medulla. The positions of recording sites were recorded as central versus peripheral medulla. Stimulating electrodes and recording carbon fibre electrodes were positioned with the aid of a 40× stereo microscope (AmScope, Irvine, Calif., USA). FSCV experiments consisted of a 60 second relaxation period for the carbon fibre in the bath followed by electrical neuronal stimulation. The electrical stimulation was carried out by driving a stimulus isolator (A356, WPI, Sarasota, Fla., USA) running in constant current mode. Stimuli were delivered to the nerve through either a platinum/iridium parallel bipolar electrode, (FHC, Bowdoin, Me., USA) or a multi-pole cuff electrode (CorTec; Freiburg Germany) as 10 µs square bipolar pulses at a constant current of 200 µA. Pulse trains were delivered at a frequency of 1 Hz, 5 Hz or 10 Hz for 60 seconds as described in the text. Both bipolar parallel and cuff electrodes limit leakage of the current and prevent stimulation of adjacent nerves compared to stimulation through unipolar electrodes and tissue grounds. Each preparation was stimulated with a single frequency, providing a single recording. Catecholamine release was then measured at 180 seconds post-stimulation.

Figure 1:
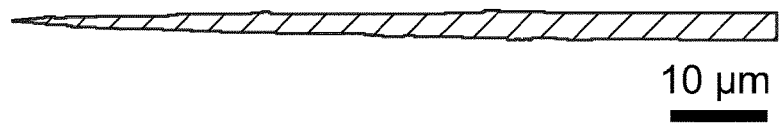
FIG. 1. Flame etched carbon fibre fast scanning cyclic voltammetry. (A) Carbon fibre electrodes were used for all fast scanning cyclic voltammetry (FSCV) recordings. The fibres are 5 μm in diameter and insulated with a parylene coating. Prior to use, each fibre was flame-etched to provide a sharp point of uninsulated carbon surface and uniform surface area. (B) The scanning command potential for FSCV recordings is shown. The scan begins with a 50 ms hold at −0.4 V to attract positively charged catecholamines to the electrode tip for detection. The scan then ramps from −0.4 V to 1.6 V and back at 40 V·s−1, covering the oxidation and reduction potentials for Epi and NE. (Ci) Resulting voltammograms for background largely capacitative currents in tris-buffered saline (grey) and the same solution containing 250 μM Epi (black) are shown. (Cii) The subtraction of background current recorded in tris-buffered saline from that containing the Epi is provided and represents the Epi-specific oxidation and reduction currents.
Figure 1:
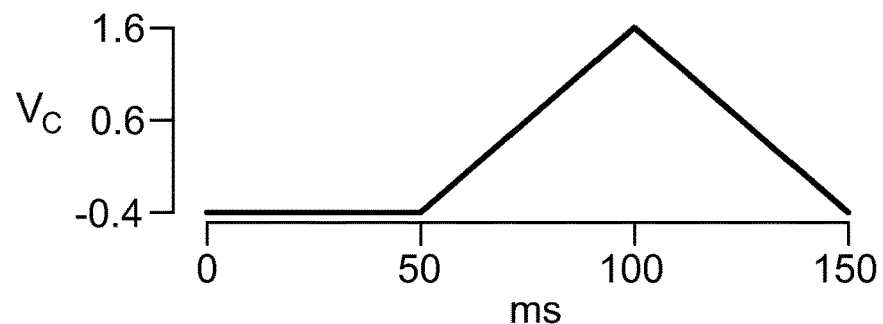
Figure 1:
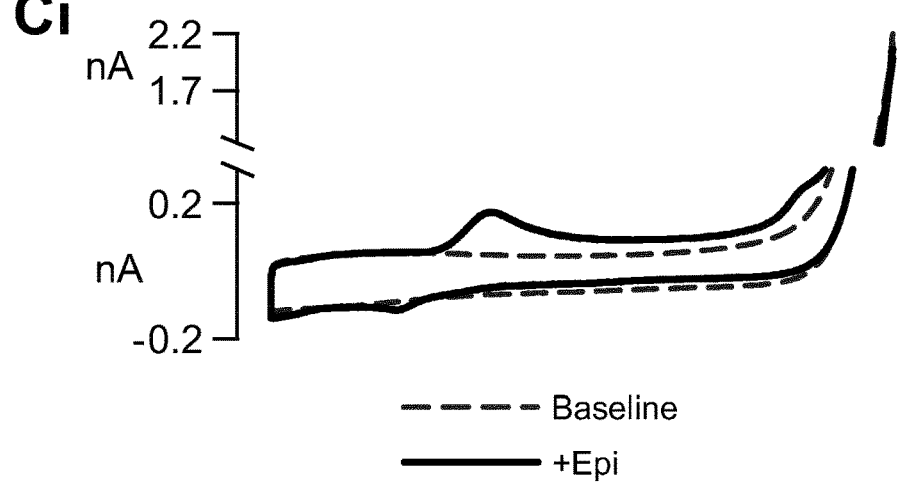
Figure 1:
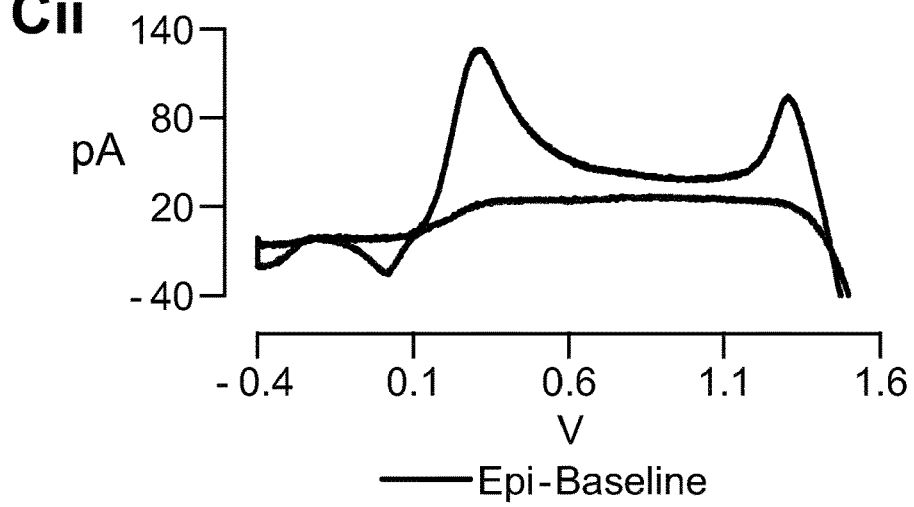

Electrode Preparation:

All electrochemical experiments were carried out with commercially-available 5 µm diameter parylene-insulated carbon fibre electrodes (CFE-2, ALA Scientific, Farmingdale, N.Y., USA). Care was taken to utilize electrodes of equivalent length throughout this study. Conventional carbon fibre amperometry or voltammetry utilizes blunt-end electrodes, generated by a transverse cut of the tip with a scalpel blade. While this approach is simple and provides excellent results for amperometric assays of quantal catecholamine release, it did not provide low-noise, fast response probes of consistent sensitivity needed for the fast scanning cyclic voltammetry utilized in this study. Therefore, we adopted a flame-etch strategy to provide low-noise, consistent fibres. Before experiments, electrodes were flame etched to remove insulation from the tip and to provide a reproducible tapered tip geometry. Flame etching was performed by submerging the carbon fibre electrode in a water bath with only a very short length extending above the surface. The tip was then flamed with an isobutane torch for 3-5 seconds. Carbon fibres were inspected under a 40× stereo microscope to ensure proper tip geometry and removal of the parylene insulation from the tip (FIG. 1A).

Data Acquisition:

Fast scanning cyclic voltammetry (FSCV) utilizes a dynamic command potential to oxidize and reduce molecules at the electrode tip. In our implementation of FSCV, the electrode was held at −0.4V for 50 ms, then ramped to 1.6 V and then back to −0.4V versus a Ag/AgCl bath ground at 40V/s (FIG. 1B). This waveform was generated and resulting digitized signal recorded through software custom written in Igor Pro (Wavemetrics, Lake Oswego, Oreg., USA) controlling a Dagan ChemClamp amplifier fitted with a 1 MOhm resistive feedback head stage (Minneapolis, Minn., USA). Data were filtered at 5 KHz through an analogue 2-pole Bessel filter prior to digitization at 20 KHz through a HEKA ITC-1600 analogue/digital converter (HEKA Instruments, Hollister, Mass., USA). Under the scanning parameters utilized in this study, both epinephrine and norepinephrine exhibit a primary oxidation potential at approximately 300 mV while epinephrine, a secondary amine, exhibits a secondary oxidation potential at approximately 1.3 V.

Results

In Vitro Fast Scanning Cyclic Voltammetry of Epinephrine vs Norepinephrine

We adapted a fast scanning cyclic voltammetry (FSCV) method for measuring separately the release of epinephrine (Epi) and norepinephrine (NE) under native neuronal stimulation. FSCV has been used to qualitatively measure release of catecholamine species from isolated bovine chromaffin cells (Pihel et al., 1994) and for the detection of bulk catecholamine release from mouse adrenal slices (Walsh et al., 2011). Here we extend this technique by calibrating signals against standard solutions and by separating signal characteristic for catecholamine species in an ex vivo, intact splanchnic-adrenal experimental preparation. In order to perform quantitative FSCV to measure epinephrine versus norepinephrine, we employed flame-etched carbon fibre electrodes (FIG. 1A, see Methods) and a command potential as described in FIG. 1B. Resulting baseline currents recorded in tris buffered saline (TBS) were largely non-specific and represent capacitative charging of the fibre, oxidation/reduction of the fibre conductive surface, and some oxidation/reduction of the bath solution. However, when solutions were supplemented with Epi or NE, additional specific components emerged within the voltammogram (FIG. 1Ci) and after baseline background subtraction, the characteristic oxidation/reduction profile for NE and Epi were readily observable (see FIG. 1Cii for an Epi subtraction example).

We measured specific oxidation profiles for both NE (FIG. 2Ai) and Epi (FIG. 2Aii) in TBS, supplemented with either catecholamine at 25, 50, 100, 250 and 500 µM. NE is a primary catecholamine and exhibits a single oxidation potential and a single reduction potential as it undergoes oxidation to an o-quinone and reduction back to norepinephrine. Epinephrine undergoes the same primary oxidation reaction and thus exhibits the same primary oxidation potential as NE. However, Epi oxidation exhibits a secondary current peak at approximately 1.3 V and a second reduction potential at approximately −0.4 V (Chen & Peng, 2003). Thus, the primary (1st) peak provides a measure of total catecholamine (NE+Epi) while the second peak provides an Epi-specific signal.

Multiple calibration parameters were obtained from voltammograms measured in standard Epi and NE solutions in vitro. The simplest parameter is the amplitude of the primary and secondary peaks in the voltammograms. Voltammograms were background subtracted as in FIG. 1 and resulting current magnitudes at the primary and secondary peak potentials are plotted for NE (FIG. 2B) or Epi (FIG. 2C) against catecholamine concentrations (see also FIG. 8 for current integrals). As expected, each peak current (primary for NE and Epi, secondary for Epi) exhibit an exponential relationship. The exponential function for the primary NE and Epi current-concentration relationships are shown as the solid lines in FIGS. 2B and C while the secondary Epi current-concentration slope is shown as the dashed line in FIG. 2C. In Epi solutions, a second parameter is the ratio of the second peak to the first (FIG. 2C, inset). This ratio is again dependent on Epi concentration and exhibits a reaction constant of 0.009 $\mu M^{-1}$; as is expected for a higher oxidation energy in the second peak. In practice, with a FSCV recording of an unknown mixture of NE and Epi, the Epi-specific component, if present, is defined by the amplitude of the current measured at the 2nd oxidation potential and conversion from pA to µM by intersection with the calibration function (FIG. 2C). The NE-specific component is calculated by dividing the 2nd Epi current amplitude by the corresponding intersection of the ratio function (FIG. 2C inset) and subtracting this value from the primary oxidation current amplitude. The resulting current is then calibrated by intersection with the NE calibration function (FIG. 2B). Yet a third parameter for calibration is the observation that the potential at which the primary 1st oxidation peak is measured, shifts with catecholamine concentration. This shift is dependent on scan rate and is only readily observed at FSCV scan rates above 20 V·s−1 (data not shown). The shift is present for both Epi and NE (FIG. 3A-B) and is thus able to be applied to mixed catecholamine solutions and serves as a complementary measure for the amplitude measurement of the primary 1st peak (0.093 mV/µM and 0.066 mV/µM for NE and Epi, respectively).

A further example of measuring the specific oxidation profiles for both NE and Epi, and deriving calibration parameters therefrom, is shown in FIGS. 2(D)-(F) and FIGS. 3(D)-(F). FIGS. 2(Di)-(Dii) show the specific oxidation profiles for both NE and Epi, respectively, in TBS, supplemented with either catecholamine at 100, 250 and 500 µM. Voltammograms were background subtracted and the resulting current magnitudes at the primary and secondary peak potentials are plotted for NE (FIG. 2E) or Epi (FIG. 2F) against catecholamine concentration. The primary NE and Epi current-concentration relationships are shown as the solid lines in FIG. 2(E)-(F), while the secondary Epi current-concentration slope is shown as the dashed line in FIG. 2(F). FIGS. 3(D)-(E) show that the potential at which the primary 1st oxidation peak is measured, shifts with catecholamine concentration.

Native Catecholamine Release from an Ex Vivo Rat Adrenal Preparation

We next set out to measure catecholamine release from the rat adrenal gland under neuronal stimulation. Toward this goal, we developed a novel ex vivo preparation. In essence, this preparation is a reduced spinal, splanchnic nerve, adrenal system maintained intact on the rear peritoneal wall of the rat (FIG. 4A, see also Methods). The preparation is bathed in an ice-chilled Ringer as described methods and pinned out.

For clarity, we provide a cartoon representation of the splanchnic nerve as it innervates the adrenal gland in FIG. 4B (see also (Celler & Schramm, 1981)). The splanchnic nerve bifurcates as it leaves the sympathetic chain ganglion, with the anterior division (AD) smaller in diameter than the posterior division. The splanchnic passes through the super-renal ganglion (SRG) where it gives rise to a small-diameter fascicle that passes to the celiac ganglion, while the majority of the fibres innervate the adrenal gland. Micrographs from the actual preparation are provided in FIG. 4, panels C and D. In FIG. 4Ci, the adrenal gland and super-renal vein can be seen in the lower half of the image. The box encompasses the innervating splanchnic nerve and is blown up in panel Cii to show both the anterior division as well as the larger posterior division. Once identified, a stimulating electrode (either a platinum/iridium parallel bipolar electrode or 2-pole cuff electrode) is placed on either the whole nerve, or either division as described below. Severing the other division served as a positive control for division-specific stimulation. The adrenal gland is hemisected at variable planes to expose the medulla and allow access to the FSCV electrodes (single electrode from the bottom in panel FIG. 4Di or dual fibres entering from below in FIG. 4Dii). This arrangement allows for division-specific stimulation of the innervating splanchnic as well as location-specific (peripheral versus central) measurement of secreted catecholamine (Epi and NE) from the gland.

Previous reports have shown like secretory isotype chromaffin cells to be organized in groups (Vollmer, 1996) that may receive common innervation (representing a functional 'adrenal unit' analogous to the well-described 'motor unit' in skeletal muscle (Feinstein et al., 1955)). Moreover, specific stressors selectively elicit epinephrine versus norepinephrine release. For example, bleeding results in greater release of epinephrine relative to norepinephrine, to facilitate blood clotting and limit blood loss (Forwell & Ingram, 1957; Goldstein, 2010). Hypoglycaemia results in elevated epinephrine release to increase hepatic blood flow as well as gluconeogenesis to elevate blood glucose levels (Vollmer et al., 1997). Conversely, cold stress results in a preferential release of norepinephrine that acts to constrict the peripheral vasculature to preserve core body heat (Vollmer, 1996). Additionally expression of either catecholamine is specific to different regions of the adrenal gland (Verhofstad et al., 1985; Ubink et al., 1995). Thus, we posed the hypothesis that specific stimulation of the anterior division versus posterior division may primarily stimulate one secretory isotype cell over the other. We tested this hypothesis by isolating either the anterior division or posterior division of the splanchnic nerve in the stimulating circuit. We then stimulated the nerve division as described and measured central versus peripheral catecholamine release from the gland. We isolated the Epi versus NE components of the catecholamine signal by the FSCV approach demonstrated in FIGS. 1-3. Data obtained for whole nerve, anterior division (AD) and posterior division (PD) stimulation at 1 Hz are presented in FIG. 5. Positive controls included severing the other unstimulated division and negative controls were conducted where the entire nerve was cut proximal to the electrode placement. The first case provided no difference from division selection through simple electrode placement and the second case showed no Epi nor NE signal (data not shown). The left column shows a schematic of the adrenal gland and locations of detected Epi (■) versus NE (□) signal for each nerve stimulation condition. It should be noted that not all recordings provided both Epi and NE recordings in either region, in which case only one symbol was contributed to the spatial release profile. Likewise, if a recording provided both Epi and NE release within a region, both a solid and empty symbol is contributed to the release map. Thus, the maps provide a summary view of the occurrence of release for Epi and NE across recordings from either central or peripheral AM.

The right column provides quantified levels of Epi (■) versus NE (□) release at the centre versus periphery of the medulla. We noted that in the whole nerve (WN) and anterior division (AD), although modest, a bias toward peripheral Epi release and central NE release was noted, although significance of this trend is not clear. No such bias was noted for the posterior division stimulation.

Next, we repeated the same recording conditions, with the exception that nerve stimulation was at 5 Hz, a frequency chosen to approximate intermediate sympathetic activity. The resulting dataset is presented in FIG. 6 and follows the same organization as that introduced in FIG. 5. As in the 1 Hz condition, we noted a bias toward peripheral Epi release and central NE release. We also noted an overall increase in total catecholamine release, but no overall significant dependence on stimulation of the whole nerve versus either branch. This dependence, however, was significantly altered upon stimulation at 10 Hz (FIG. 7), a firing level chosen to mimic sympathetic activation. Under this condition, we again noted a bias toward peripheral Epi secretion and central NE release. We also noted a further increase in total catecholamine release from the adrenal gland. However, compared to previous stimulation paradigms, 10 Hz stimulation resulted in a dramatically elevated Epi release under whole nerve stimulation. Moreover, the stark elevation in peripheral Epi release was notably abolished by stimulating just one of the two divisions. Leaving either the posterior or the anterior division out of the stimulation path resulted in a failure to recruit the dramatic increase in peripheral Epi exocytosis (Table 1, see also table 2 for numerical concentration values for all conditions). Thus, it appears that while no specificity on either branch for release of Epi versus NE exists, what appears to be is that excitation of the entire nerve is required to support the surge in epinephrine release observed under heightened sympathetic firing. Previous reports have surmised the differential stimulus-secretion behaviour for NE versus Epi must be due to differential descending efferent nerve tracts (Edwards et al., 1996; Vollmer, 1996). Our data indicate that by the time the splanchnic passes through the sympathetic chain ganglion, the splanchnic fibres within either division are a mixed population (Strack et al., 1988). The findings reported are novel in that they further define that Epi-secreting cells express a higher stimulation threshold and require a larger number of active innervating fibres for maximal excitation.

Once brought to threshold, Epi-secreting cells also exhibit a steeper stimulus-secretion function than NE-secreting cells.

TABLE 1

Normalized Peripheral Catecholamine Release

|  | 1 Hz | | 5 Hz | | 10 Hz | |
| --- | --- | --- | --- | --- | --- | --- |
|  | Epi | NE | Epi | NE | Epi | NE |
| WN (8) | 1 ± 0.42 | 1 ± 0.24 | 1 ± 0.32 | 1 ± 0.13 | 1 ± 0.27 | 1 ± 0.15 |
| AD (7) | 1.8 ± 0.61 | 0.78 ± 0.15 | 1.15 ± 0.28 | 1.17 ± 0.20 | 0.15 ± 0.07* | 0.81 ± 0.12 |
| PD (7) | 1.03 ± 0.33 | 0.92 ± 0.22 | 0.94 ± 0.37 | 1.47 ± 0.28 | 0.32 ± 0.07* | 0.67 ± 0.10 |

Table 1. Peripheral Epi or NE release was measured under each frequency and for each nerve stimulation condition. Each recording is from a single preparation. All values, Whole Nerve (WN), Anterior Division (AD) and Posterior Division (PD), were normalized internally to the Whole Nerve (WN) stimulation condition to allow for comparison. Numbers of recordings for each condition (WN, AD and PD) are supplied in parentheses. The only frequency that exhibited a statistically significant dependence on nerve fascicle integrity was Epi release at 10 Hz stimulation, with either AD or PD-specific stimulation exhibiting a significant decrease in output compared to WN stimulation. Statistical analysis compared each condition (AD, PD) for a given stimulation frequency against the matched WN control value. Significance was determined by a paired Student's t-test with a barrier of $p<0.05$ (stared cells, $p=0.01$ and $p=0.03$ for 10 Hz AD and PD, respectively).

TABLE 2

Raw Catecholamine Values for all Conditions ($\mu$M).

| Nerve | | Whole | Anterior | Posterior |
| --- | --- | --- | --- | --- |
| Epinephrine | | | | |
| Center | 1 Hz | 4.59 ± 1.93 (8) | 6.89 ± 2.71 (7) | 3.62 ± 0.8 (7) |
|  | 5 Hz | 6.22 ± 2.13 (14) | 3.91 ± 1.69 (7) | 10.49 ± 5.56 (7) |
|  | 10 Hz | 8.56 ± 1.82 (12) | 9.85 ± 5.56 (10) | 8.57 ± 5.23 (8) |
| Peripheral | 1 Hz | 7.41 ± 3.16 (8) | 13.33 ± 4.53 (7) | 7.64 ± 2.44 (7) |
|  | 5 Hz | 13.09 ± 4.20 (14) | 15.11 ± 3.71 (7) | 12.36 ± 4.91 (7) |
|  | 10 Hz | 70.29 ± 19.27 (12) | 10.67 ± 5.26 (10) | 22.86 ± 5.08 (8) |
| Norepinephrine | | | | |
| Center | 1 Hz | 64.46 ± 16.20 (8) | 45.28 ± 10.76 (7) | 40.38 ± 14.40 (7) |
|  | 5 Hz | 48.96 ± 7.78 (14) | 43.36 ± 6.97 (7) | 35.31 ± 11.72 (7) |
|  | 10 Hz | 88.32 ± 4.10 (12) | 56.31 ± 10.11 (10) | 55.76 ± 8.25 (8) |
| Peripheral | 1 Hz | 48.15 ± 11.35 (8) | 37.5 ± 7.14 (7) | 44.29 ± 10.75 (7) |
|  | 5 Hz | 31.12 ± 4.00 (14) | 36.42 ± 6.29 (7) | 45.78 ± 8.69 (7) |
|  | 10 Hz | 60.76 ± 9.04 (12) | 49.72 ± 8.15 (10) | 40.67 ± 6.13 (8) |

Table 2. Numeric values for all stimulation conditions are provided. Data are supplied as mean measured catecholamine detected (in $\mu$M)±S.E.M. Numbers of recordings for each condition are supplied in parentheses.

Discussion

In this study, we utilized highly sensitive, fast scanning cyclic voltammetry to specifically measure Epi versus NE release from the adrenal medulla. It should be noted that the calibration method used in this data set was intended to allow for quantitative comparison of catecholamine release across several stimulation parameters. It is clear that the concentrations presented are not analogous to those observed in serum under stress, where there is a significant dilution factor. We employed a novel ex vivo splanchnic-adrenal preparation to test for native neuronal stimulation of epinephrine versus norepinephrine in an activity-dependent manner. We also mapped the tissue-level organization of adrenal Epi and NE release within the gland. Using this experimental system, we tested the potential that the anterior and posterior divisions of the splanchnic nerve represent a functional separation in the innervating pathway responsible for Epi versus NE release. While this was not found to be true, we did find that Epi and NE are indeed show preferential released from different regions within the adrenal medulla. Norepinephrine release tends to occur from the central portion of the medulla while epinephrine tends to be released from the periphery. Moreover, we find that NE release increases through a range of nerve firing rates while Epi expresses a steep increase in release only under the highest firing rates. This steep release function is only observed under whole nerve stimulation; stimulating either branch in isolation does not express the steep increase in Epi release.

Previous studies have demonstrated that epinephrine and norepinephrine-secreting cells are innervated by calretinin-negative and positive fibres respectively, and that calretinin-positive fibres are predominant in the rostral portion of the spinal cord (Edwards et al., 1996). Due to its relative caudal position, it would be expected that the anterior division of the splanchnic may include a lower proportion of calretinin-positive nerve fibres, and thus preferentially stimulate epinephrine-secreting chromaffin cells. This was not observed, indicating that these specific fibre tracts mix and lose anatomic organization prior to, or as the nerve exits the spinal cord. It may be that neurons in the spinal cord are activated in a stressor-specific manner from various central control circuits (Strack et al., 1988; Cao & Morrison, 2001), integrate them, and output a signal determined by activation of specific calretinin-positive or negative nerve fascicles, innervating specific patches of cells in the adrenal medulla. In this way, selective catecholamine release could be determined, with whole adrenal units (clusters of like isotype chromaffin cells) modulated by paracrine effects of catecholamines (Kajiwara et al., 1997; Brede et al., 2003) and potentially neuropeptide release (Aunis, 1998).

Thus it seems that the splanchnic nerve does not follow an anatomical organization with respect to the branches. Each branch must be a mixed population of NE and Epi-innervating fibres. Moreover, the data provided here demonstrate that the higher stimulus threshold for Epi versus NE secretion follows a simple capacity function; it does not matter which division of the splanchnic is stimulated or cut, maximal recruitment of Epi-secretion capacity is lost by eliminating splanchnic nerve fibres, no matter their location. Maximal Epi section is only achieved with all possible nerve fibres participating. The surge in epinephrine shown under the sympatho-adrenal stress reflex is due to a higher threshold, steeper stimulus-secretion function than that for norepinephrine.

Adrenal chromaffin cells are poly-innervated, receiving between 1 and 4 synaptic contacts each. It is not known whether this heterogeneity in poly-innervation correlates with cell isotype. Previous studies have shown that Epi- and NE-secreting chromaffin cells have different numbers of synapses (Iijima et al., 1992; Kajiwara et al., 1997), which may provide an additional potential explanation for our observations. If NE-secreting cells are preferentially innervated by more splanchnic terminals than Epi-secreting cells, they may be expected to exhibit catecholamine release under modest splanchnic stimulation due to simultaneous excitatory inputs. Likewise, only after more intense splanchnic firing, are the Epi-secreting cells brought to threshold for excitation and secretion. This potential model will require further testing through histological and electrophysiological investigation of synapse number and synaptic excitation in chromaffin cells. Lastly, accessory transmitters other than acetylcholine are released from the splanchnic terminals that act as strong secretagogues for chromaffin cell catecholamine release. Pituitary adenylyl cyclase activating peptide (PACAP) is released specifically under elevated sympathetic firing and evokes the stress-associated surge in adrenal catecholamine release (Hamelink et al., 2002; Kuri et al., 2009; Smith & Eiden, 2012). Future experiments will need to address this point. It may be that splanchnic efferents innervating Epi- versus NE-secreting cells express different levels of PACAP or that Epi- versus NE-secreting cells exhibit differential sensitivity to splanchnic PACAP release through receptor expression. These possible mechanisms for the differing stimulus-secretion relationship in Epi- versus NE-secreting cells also will require significant investigation for determination of the potential molecular basis of stressor-specific catecholamine release.

Summary

Activation of the acute sympatho-adrenal stress response evokes release of epinephrine and norepinephrine from the adrenal medulla into the circulation. Specific stressors favour either epinephrine or norepinephrine release to meet specific physical demands. The sympathetic splanchnic nerve bifurcates into an anterior and posterior division as it innervates the adrenal medulla. We tested the hypothesis that selective epinephrine versus norepinephrine release is due to a functional segregation of sympathetic efferent innervation through the divisions of the splanchnic nerve. Epinephrine release is specifically enhanced from the periphery of the gland under elevated stimulation. This recruitment of Epinephrine release is only supported by stimulation of the whole nerve and is lost by specific stimulation of one or the other divisions alone. These data provide the first functional anatomical mechanism for stress-evoked differential epinephrine versus norepinephrine release from the adrenal medulla and is useful for control of epinephrine release under stress.

REFERENCES

Brede M, Nagy G, Philipp M, Sorensen J B, Lohse M J & Hein L. (2003). Differential control of adrenal and sympathetic catecholamine release by alpha 2-adrenoceptor subtypes. Mol Endocrinol 17, 1640-1646.

Cao W H & Morrison S F. (2001). Differential chemoreceptor reflex responses of adrenal preganglionic neurons. Am J Physiol Regul Integr Comp Physiol 281, R1825-1832.

Carbonaro D A, Mitchell J P, Hall F L & Vulliet P R. (1988). Altered reactivity of the rat adrenal medulla. Brain Res Bull 21, 451-458.

Carmichael S W. (1986). Morphology and innervation of the adrenal medulla. In Stimulus-Secretion Coupling, Vol 1, ed. Rosenheck K & Lelkes P, pp. 40-49. CRC, Boca Raton, Fla.

Carmichael S W & Winkler H. (1985). The adrenal chromaffin cell. Sci Am 253, 40-49.

Celler B G & Schramm L P. (1981). Pre- and postganglionic sympathetic activity in splanchnic nerves of rats. Am J Physiol 241, R55-61.

Chen S & Peng K. (2003). The electrochemical properties of dopamine, epinephrine, norepinephrine, and their electrocatalytic reactions on cobalt(II) hexacyanoferrate films. J Electroanal Chem 547, 179-189.

Coupland R E. (1958). The effects of insulin, reserpine and choline 2:6-xylylether bromide on the adrenal medulla and on medullary autografts in the rat. J Endocrinol 17, 191-196.

Cryer P E. (1980). Physiology and pathophysiology of the human sympathoadrenal neuroendocrine system. N Engl J Med 303, 436-444.

Damase-Michel C, Tavernier G, Giraud P, Montastruc J L, Montastruc P & Tran M A. (1993). Effects of clonidine, dihydralazine and splanchnic nerve stimulation on the release of neuropeptide Y, MET-enkephalin and catecholamines from dog adrenal medulla. Naunyn Schmiedebergs Arch Pharmacol 348, 379-384.

Edwards S L, Anderson C R, Southwell B R & McAllen R M. (1996). Distinct preganglionic neurons innervate noradrenaline and adrenaline cells in the cat adrenal medulla. Neuroscience 70, 825-832.

Feinstein B, Lindegard B, Nyman E & Wohlfart G. (1955). Morphologic studies of motor units in normal human muscles. Acta Anat (Basel) 23, 127-142.

Forwell G D & Ingram G I. (1957). The effect of adrenaline infusion on human blood coagulation. J Physiol 135, 371-383.

Gerich J E, Karam J H & Forsham P H. (1973). Stimulation of glucagon secretion by epinephrine in man. J Clin Endocrinol Metab 37, 479-481.

Glaviano V V, Bass N & Nykiel F. (1960). Adrenal medullary secretion of epinephrine and norepinephrine in dogs subjected to hemorrhagic hypotension. Circ Res 8, 564-571.

Goldstein D S. (2010). Adrenal responses to stress. Cell Mol Neurobiol 30, 1433-1440.

Goldstein D S, McCarty R, Polinsky R J & Kopin I J. (1983). Relationship between plasma norepinephrine and sympathetic neural activity. Hypertension 5, 552-559.

Goldstein M, Fuxe K, Hokfelt T & Joh T H. (1971). Immunohistochemical studies on phenylethanolamine-N-methyltransferase, dopa-decarboxylase and dopamine-hydroxylase. Experientia 27, 951-952.

Habib K E, Gold P W & Chrousos G P. (2001). Neuroendocrinology of stress. In Endocrinol Metab Clin North Am, pp. 695-728; vii-viii.

Hamelink C, Tjurmina O, Damadzic R, Young W S, Weihe E, Lee H W & Eiden L E. (2002). Pituitary adenylate cyclase-activating polypeptide is a sympathoadrenal neurotransmitter involved in catecholamine regulation and glucohomeostasis. Proc Natl Acad Sci USA 99, 461-466.

Henry J P. (1992). Biological basis of the stress response. Integr Physiol Behav Sci 27, 66-83.

Iijima T, Matsumoto G & Kidokoro Y. (1992). Synaptic activation of rat adrenal medulla examined with a large photodiode array in combination with a voltage-sensitive dye. Neuroscience 51, 211-219.

Jeong K H, Jacobson L, Pacak K, Widmaier E P, Goldstein D S & Majzoub J A. (2000). Impaired basal and restraint-induced epinephrine secretion in corticotropin-releasing hormone-deficient mice. Endocrinology 141, 1142-1150.

Kajiwara R, Sand O, Kidokoro Y, Barish M E & Iijima T. (1997). Functional organization of chromaffin cells and cholinergic synaptic transmission in rat adrenal medulla. Jpn J Physiol 47, 449-464.

Kawagoe K T, Jankowski J A & Wightman R M. (1991). Etched carbon-fiber electrodes as amperometric detectors of catecholamine secretion from isolated biological cells. Anal Chem 63, 1589-1594.

Klevans L R & Gebber G L. (1970). Comparison of differential secretion of adrenal catecholamines by splanchnic nerve stimulation and cholinergic agents. J Pharmacol Exp Ther 172, 69-76.

Krentz A J, Freedman D, Greene R, McKinley M, Boyle P J & Schade D S. (1996). Differential effects of physiological versus pathophysiological plasma concentrations of epinephrine and norepinephrine on ketone body metabolism and hepatic portal blood flow in man. Metabolism 45, 1214-1220.

Kumar G K, Rai V, Sharma S D, Ramakrishnan D P, Peng Y J, Souvannakitti D & Prabhakar N R. (2006). Chronic intermittent hypoxia induces hypoxia-evoked catecholamine efflux in adult rat adrenal medulla via oxidative stress. J Physiol 575, 229-239.

Kuri B A, Chan S A & Smith C B. (2009). PACAP regulates immediate catecholamine release from adrenal chromaffin cells in an activity-dependent manner through a protein kinase C-dependent pathway. J Neurochem 110, 1214-1225.

Kvetnansky R, Lu X & Ziegler M G. (2013). Stress-triggered changes in peripheral catecholaminergic systems. Advances in pharmacology 68, 359-397.

Leszczyszyn D J, Jankowski J A, Viveros O H, Diliberto E J, Jr., Near J A & Wightman R M. (1991). Secretion of catecholamines from individual adrenal medullary chromaffin cells. J Neurochem 56, 1855-1863.

Marley E & Prout G I. (1965). Physiology and pharmacology of the splanchnic-adrenal medullary junction. J Physiol 180, 483-513.

Moyer J H & Mills L C. (1975). Vasopressor agents in shock. Am J Nurs 75, 620-625.

Pihel K, Schroeder T J & Wightman R M. (1994). Rapid and Selective Cyclic Voltammetric Measurements of Epinephrine and Norepinephrine as a Method To Measure Secretion from Single Bovine Adrenal Medullary Cells. Anal Chem 66, 4532-4537.

Robertson D, Johnson G A, Robertson R M, Nies A S, Shand D G & Oates J A. (1979). Comparative assessment of stimuli that release neuronal and adrenomedullary catecholamines in man. Circulation 59, 637-643.

Scheurink A & Ritter S. (1993). Sympathoadrenal responses to glucoprivation and lipoprivation in rats. Physiol Behav 53, 995-1000.

Smith C B & Eiden L E. (2012). Is PACAP the major neurotransmitter for stress transduction at the adrenomedullary synapse? J Mol Neurosci 48, 403-412.

Strack A M, Sawyer W B, Marubio L M & Loewy A D. (1988). Spinal origin of sympathetic preganglionic neurons in the rat. Brain Res 455, 187-191.

Ubink R, Lange W & Verhofstad A. (1995). Simultaneous immunoenzymatic staining of catecholamines, catecholamine-biosynthesizing enzymes, and bromodeoxyuridine in adrenal medullary cells of the rat. J Histochem Cytochem 43, 39-46.

Verhofstad A A, Coupland R E, Parker T R & Goldstein M. (1985). Immunohistochemical and biochemical study on the development of the noradrenaline- and adrenaline-storing cells of the adrenal medulla of the rat. Cell Tissue Res 242, 233-243.

Vollmer R R. (1996). Selective neural regulation of epinephrine and norepinephrine cells in the adrenal medulla—cardiovascular implications. Clin Exp Hypertens 18, 731-751.

Vollmer R R, Balcita J J, Sved A F & Edwards D J. (1997). Adrenal epinephrine and norepinephrine release to hypoglycemia measured by microdialysis in conscious rats. Am J Physiol 273, R1758-1763.

Vollmer R R, Baruchin A, Kolibal-Pegher S S, Corey S P, Stricker E M & Kaplan B B. (1992). Selective activation of norepinephrine- and epinephrine-secreting chromaffin cells in rat adrenal medulla. Am J Physiol 263, R716-721.

Walsh P L, Petrovic J & Wightman R M. (2011). Distinguishing splanchnic nerve and chromaffin cell stimulation in mouse adrenal slices with fast-scan cyclic voltammetry. Am J Physiol Cell Physiol 300, C49-57.

The invention claimed is:

1. A device or system for modulating the neural activity of a branch of the greater splanchnic nerve (GSN) between the suprarenal ganglion and the adrenal gland in a subject, the device or system comprising: at least one transducer suitable for placement on or around the whole branch of the GSN between the suprarenal ganglion and the adrenal gland or a division of the branch of the GSN between the suprarenal ganglion and the adrenal gland, and a signal generator for generating at least one signal to be applied to the branch of the GSN between the suprarenal ganglion and the adrenal gland via the at least one transducer such that the at least one signal inhibits the neural activity of the branch of the GSN between the suprarenal ganglion and the adrenal gland to produce a physiological response in the subject, wherein the physiological response is a decrease in the secretion of epinephrine (Epi), norepinephrine (NE), or enkephalin from the adrenal medulla, and wherein the at least one transducer is at least one electrode, and the signal generator is a voltage or current source configured to generate an electrical signal to be applied to the branch of the GSN between the suprarenal ganglion and the adrenal gland via the at least one electrode, and wherein the stimulation electrical signal has a frequency of between 1 Hz and 10 Hz.

2. The device or system of claim 1, wherein the at least one transducer is at least one electrode, and the signal generator is a voltage or current source configured to generate an electrical signal to be applied to the branch of the GSN between the suprarenal ganglion and the adrenal gland, via the at least one electrode.

3. The device or system of claim 2, wherein the signal generator is configured to generate an electrical inhibition signal adapted to inhibit neural activity in the branch of the GSN between the suprarenal ganglion and the adrenal gland.

4. The device or system of claim 3, wherein the signal generator is configured to apply a first signal to the first transducer independently of the second transducer, wherein the first and/or second signal is an electrical inhibition signal adapted to inhibit neural activity in the branch of the GSN supplying the adrenal gland.

5. A method of reversibly modulating neural activity in a branch of the GSN supplying the adrenal gland, comprising: (i) implanting in the subject a device or system of claim 1; positioning the transducer in signaling signalling contact with the branch of the GSN between the suprarenal ganglion and the adrenal gland.

6. A device or system for modulating the neural activity of a branch of the greater splanchnic nerve (GSN) supplying the adrenal gland in a subject between the suprarenal ganglion and the adrenal gland in a subject, the device or system comprising: a first transducer suitable for placement on or around the anterior division of the branch of the GSN, a second transducer suitable for placement on or around the posterior division of the branch of the GSN, and a signal generator for generating at least one signal to be selectively applied to the GSN division(s) via the first and/or second transducers respectively such that the at least one signal inhibits the neural activity of the GSN division(s) to produce a physiological response in the subject, wherein the physiological response is a decrease in secretion of epinephrine (Epi), norepinephrine (NE) or enkephalin from the adrenal medulla.

7. The device or system of claim 6, wherein the signal generator is configured to generate a first signal to be applied via the first transducer, and a second signal to be applied via the second transducer, wherein the first signal is different from the second signal.

8. The device or system of claim 6, wherein the signal generator is configured to apply a first signal to the first transducer independently of the second transducer.

9. A method of treating a norepinephrine-related pathology, a epinephrine-related pathology, an enkephalin-related pathology, or a condition associated with impaired control of adrenal medullary secretion, such as impaired catecholamine and/or enkephalin control, comprising applying at least one signal to a branch of the greater splanchnic nerve (GSN) supplying the adrenal gland in a subject, preferably the branch of the GSN between the suprarenal ganglion and the adrenal gland, via at least one transducer that is suitable for placement on or around a GSN branch, such that the at least one signal inhibits the neural activity of the GSN branch to produce a physiological response in the subject, wherein the physiological response is a decrease in secretion of signaling molecules from the adrenal medulla, and wherein the at least one transducer is at least one electrode, and the signal is an electrical signal to be applied to the GSN branch via the at least one electrode, and wherein the stimulation electrical signal has a frequency of between 1 Hz and 10 Hz.

* * * * *